United States Patent [19]

Pettit

[11] Patent Number: 5,099,504
[45] Date of Patent: Mar. 24, 1992

[54] THICKNESS/DENSITY MESURING APPARATUS

[75] Inventor: John W. Pettit, Derwood, Md.

[73] Assignee: Adaptive Technologies, Inc., Gaithersburg, Md.

[21] Appl. No.: 341,776

[22] Filed: Apr. 21, 1989

Related U.S. Application Data

[63] Continuation-in-part of Ser. No. 267,646, Nov. 4, 1988, abandoned, which is a continuation of Ser. No. 32,639, Mar. 31, 1987, abandoned.

[51] Int. Cl.$^5$ .................... G01B 15/02; G01N 23/06; G01T 1/22; G01T 1/24
[52] U.S. Cl. ........................................ 378/54; 378/56; 250/370.14
[58] Field of Search ............ 378/54, 55, 56, 89; 250/308, 358.1, 359.1, 370.01, 370.14

[56] References Cited

U.S. PATENT DOCUMENTS

| | | | |
|---|---|---|---|
| 2,879,399 | 3/1959 | Friedman | 378/56 X |
| 3,016,460 | 1/1962 | Andresen | 425/141 X |
| 3,611,173 | 10/1971 | Goulding et al. | 330/59 |
| 3,828,190 | 8/1974 | Dahlin et al. | 250/308 |
| 3,936,665 | 2/1976 | Donoghue | 364/469 |
| 3,974,248 | 8/1976 | Atkinson | 425/141 X |
| 4,047,029 | 9/1977 | Allport | 378/90 |
| 4,178,509 | 12/1979 | More et al. | 378/161 |
| 4,212,534 | 7/1980 | Bodlaj | 356/1 |
| 4,271,477 | 6/1981 | Williams | 364/563 |
| 4,292,645 | 9/1981 | Schlosser et al. | 250/370.09 X |
| 4,301,366 | 11/1981 | Bertin et al. | 250/308 |
| 4,307,050 | 12/1981 | Greter | 425/141 X |
| 4,409,160 | 10/1983 | Kogo et al. | 425/141 X |
| 4,427,892 | 1/1984 | Malcolme-Lawes et al. | 250/308 X |
| 4,447,721 | 5/1984 | Wang | 378/161 X |
| 4,514,348 | 4/1985 | Iguchi et al. | 425/141 X |
| 4,555,767 | 11/1985 | Case et al. | 364/563 |
| 4,569,717 | 2/1986 | Ohgami et al. | 356/72 X |
| 4,574,387 | 3/1986 | Gignoux et al. | 378/56 |
| 4,578,647 | 3/1986 | Sasamura | 330/253 |
| 4,620,321 | 10/1986 | Chown | 455/619 |
| 4,682,034 | 7/1987 | Sarnt et al. | 250/308 X |
| 4,731,804 | 3/1988 | Jenkins | 378/161 X |
| 4,777,362 | 10/1988 | Faris | 250/308 X |
| 4,785,186 | 11/1988 | Street et al. | 250/370.01 X |

FOREIGN PATENT DOCUMENTS 2118846  4/1972  France ............................ 250/370 K

OTHER PUBLICATIONS

Hamamatsu Technical Data Sheet No. S-504-01, "Large-Area PIN Silicon Photodiodes for Scintillation Detection and Precision Photometry", Jun. 1986.
Hamamatsu, The Latest Photonic Devices for Nuclear Science, Oct. 1985.
Hamamatsu Technical Data Sheet "10×10mm$^2$ Sensitive Area PIN Silicon Photocells S1723, S1790 Series".
"Extrusion", Plastic Technology, vol. 34, No. 8, Aug. 1988, p. 65.
Hamamatsu Technical Data Sheet, "PIN Silicon Photocells S1722, S1863", 1984.
Bioscan, "Quick-Count, A New Concept in Radioisotope Counting", Nov. 1984.
Sheather, "The Support of Thin Windows . . . Counters", J. Phys. E. (GB), vol. 6, No. 4, Apr. 1973.
Tomimasu et al., "Junction-FET Dosimeter", J. of Applied Phys., vol. 47, No. 4, Apr. 1976.

Primary Examiner—Eugene R. LaRoche
Assistant Examiner—Seung Ham
Attorney, Agent, or Firm—Dickstein, Shapiro & Morin

[57] ABSTRACT

A low-voltage, compact measuring apparatus for measuring any one of thickness, density and denier of a material is disclosed which uses a PIN diode in conjunction with a low noise processing circuit to detect particle radiation emitted from a source, which source has its detection intensity affected by a material to be measured. A light blocking, particle radiation permeable material protects the PIN diode from detecting light radiation. A system for controlling the extrusion of a film using the measuring apparatus, and for correcting for erroneous measurement caused by web flutter, are also disclosed.

36 Claims, 12 Drawing Sheets

THICKNESS/DENSITY MESURING APPARATUS

This application is a continuation-in-part application of Ser. No. 267,646, filed Nov. 4, 1988, which in turn is a continuation of Ser. No. 032,639 filed Mar. 31, 1987, now abandoned.

BACKGROUND OF THE INVENTION

1. Field of the Invention

The present invention relates to a thickness or density measuring apparatus which is particularly adapted to measure the thickness or density of a film. The invention has particular, though not exclusive, utility in the plastics processing industry where thickness and/or density of an extruded plastic film must be controlled to production tolerances. The invention can also be used to measure the denier of a fiber.

2. Description of the Prior Art

Thickness and/or density measuring systems are known in the art which rely on various types of sensors for a measurement. For thickness measurements, mechanical gauge-type devices are known which contact with the material or object to be measured and which provide a thickness readout which can be used to control apparatus for manufacturing the material and/or object to insure that a desired thickness is obtained. Likewise, density measuring devices are known in which the density of an object is measured usually by passing radiation through the object. Changes in density are seen by changes in the transmittance of the radiation through the object.

In many production environments particularly where plastic films and sheets are being manufactured, the control over material usage and quality of the product is greatly enhanced when the thickness of the material can be accurately measured. This is especially true when the measurement can be made in an on-line manner where the measurement instrument can be installed on or quite close to the producing machinery and the thickness information can be used in a feedback control system for the process so that optimum parameters can be determined for the machinery to produce a desired film product. In such an environment the output of the measuring instrument must respond quickly to thickness variations, and the output is fed back electronically or mechanically to control machinery without any human intervention. In order to do this, the instrument must be inherently rugged to withstand the harshness of the production environment, be small enough in size to be able to fit where the measurement is most needed, and have minimal input and output connections so that integration with computing and control equipment can be facilitated.

At present, many thickness measurements are made using the principles of detection of nuclear and atomic particle radiation emitted from a source. U.S. Pat. No. 4,047,029 is representative and discusses various radiation sources including those producing beta particles, X-rays and gamma rays. These rays are attenuated or scattered when they pass through a material as a consequence of their interaction with the atoms and nuclei in the material. The amount of interaction is dependent on the number of atoms and nuclei in the path of the radiation and the tendency of the material to interact with the type of radiation striking it. For a given material and type of radiation the amount of interaction will depend on the material's density and thickness since density determines the number of atoms and nuclei in the path of the radiation per unit volume and thickness determines the length of the travel when the radiation is made to pass through the material, usually at right angles to a flat surface.

Present generation thickness measuring devices based on the principles of particle detection will detect and count individually particles that pass through a sample of a material and compare the count rate observed for an unknown sample with a count rate observed with a sample of known thickness. The material thickness is then inferred by assuming similar density between the known and unknown samples and applying, typically, a linear relationship between the count rate and material thickness. The relationship is typically not linear over a very large range but can usually be assumed to be linear over the range of thicknesses encountered in a production environment, without significant loss of accuracy.

The method currently employed for detecting such radiation works through the use of a scintillation detector or a gas filled ionization counter. The ionization counter consists of a chamber of gas which can be made to ionize by the radiation and the resulting electric charge is collected through the use of a high voltage between the chamber wall and a thin wire in the center of the chamber. Ionized pairs of electrons and atoms are drawn to the opposite polarity, which will be the wall or the wire, depending how the voltage is applied, under the influence of the resulting electric field. This charge is then collected and amplified as a signal in a charge sensitive amplifier and then may be compared to a voltage threshold to determine whether a valid detection has been made. A disadvantage of an ionization chamber in a production environment is that the gas may leak out of the chamber or may break down and degrade through use and the chamber is usually quite large to achieve efficiency, making it difficult to apply to many environments. Moreover, the ionization chamber requires a very high voltage, typically in the range of 1,000 to 3,000 volts, and is also costly which further inhibits its widespread use as a thickness measuring device.

The scintillation detector, which is also known in the art to measure thickness, uses a material called a scintilator, which when it absorbs a unit of radiation becomes activated and will deactivate by giving off light in the ultraviolet range through the process of scintillation. This ultraviolet light is then detected by a quite sensitive light detector known as a photomultiplier tube. The photomultiplier tube is closely coupled to the scintillator material so that ultraviolet light will pass into it. A detection signal from a first photocathode within the photomultiplier tube is typically multiplied by a series of dynode stages which are successively more positive in charge than the preceding dynode stage. The multiplied signal is then taken as an output signal. A disadvantage of the scintillation detector is that it also uses lethal high voltages in the 1,000 to 3,000 volt range and in addition the photomultiplier tube characteristics change and drift with use and age and with fluctuations in the high voltage level. This type of a detector is also prone to breakage since it is an evacuated glass tube and because of its size, weight and cost this type of detector also cannot be used in many types of environments.

Semiconductor diode particle detectors are also known. They consist of a p-type layer, an n-type layer and an optional intrinsic layer in the middle. This diode is sensitive to light and nuclear and atomic radiation when the same strikes the diode. Detectors of this type have been used for high resolution nuclear spectroscopy. The signal generated by this type of detector consists of the collection of charge released when the radiation loses energy in the sensitive region of the detector. This charge is collected across the p-type and n-type materials and is amplified with a high performance charge sensitive amplifier.

Typically these types of detection devices have a very small output signal. The output signal is so small that noise generated by thermal effects or impurities and imperfections in the silicon material will overcome the charge signal. For this reason, such detectors are typically operated at quite low temperatures, usually through the use of a liquid nitrogen coolant to arrive at adequate performance. While this type of detector could be used in laboratory research, it cannot be practically used in a production environment.

SUMMARY OF THE INVENTION

One object of the invention is the provision of a small compact, rugged and low cost particle radiation detecting thickness/density measuring system.

Another object of the invention is the provision of a particle radiation detecting thickness/density measuring system which operates on low voltages.

Another object of the invention is the provision of a particle radiation detecting thickness/density measuring device which can have separable parts, one including a detection head containing those elements necessary for detecting and registering particle counts and another processing and display section located elsewhere for monitoring the thickness/density measurement with a simple low voltage cable passing between the two.

An additional object of the invention is the provision of a portable low-cost particle radiation detecting thickness/density measuring apparatus which provides a fixed gap between a radiation source and detection head in which a material of unknown thickness can be placed for measurement.

Another object of the invention is the provision of a control system for monitoring and controlling the thickness of an extruded film during its production using a plurality of simple, low cost particle radiation detecting thickness measuring devices.

An additional object of the invention is the provision of a particle radiation detecting coating thickness measuring system which operates to measure the thickness of a coating layer applied to a base layer or substrate.

An additional object of the invention is the provision of a particle radiation detecting flutter compensation system for compensating for material web thickness or density measurement errors caused by flutter of the web under measurement.

An additional object of the invention is the provision of a particle radiation detecting yarn or fiber denier measurement system The present invention makes particular use of a new type of silicon diode detector which contains a p-layer, an n-layer and an intrinsic layer between them and which is operable at room temperature to detect radiation. The device, termed a PIN diode, is primarily intended for detection of laser and ultraviolet light, but it has also been discovered that this detector is also sensitive to nuclear and atomic radiation such as beta particles, X-rays and gamma rays.

The invention employs the PIN diode in a particular mechanical and circuit configuration to enhance its ability to detect particle radiation only. A light blocking window is used to screen the PIN diode from the effects of light radiation while the output signal therefrom is connected to a charge sensitive preamplifier. A high quality amplifier is then connected to the output of the preamplifier to develop a suitable signal which can be provided to a threshold detector, the output of which is sent to a pulse rate counter. The output of the pulse rate counter can be used together with pulse rate information derived during previous calibration use of the invention for a material of known thickness to determine a thickness measurement from a detected pulse rate when a material of unknown thickness is provided in the path of the radiation from a source to the PIN diode detector. Similar calibration and detection steps can be used to employ the invention as a density measuring device, or as a device for measuring the denier of a fiber or yarn.

The PIN diode used in the invention is also preferably surrounded by electrical shielding, which is grounded, preferably to the grounding point of the charge sensitive preamplifier, to minimize spurious signal effects which may affect the relatively low output signal of the PIN diode.

By using the PIN diode and associated small scale electronics package, a small compact detector can be provided which will allow it to be used in many applications that present generation thickness measuring devices based on the principle of particle radiation cannot approach. Typically, such a detector could be used in profile extrusion, blown film and blow molding, as well as the typical areas such as sheet and film extrusion. Moreover, since the measurement instrument of the invention requires only low voltage circuits, there is no safety hazard and associated heavily insulated power cables and connections are avoided thereby opening up new installation possibilities over present day equipment. Still further, the small size and compact solid state construction can provide high reliability and stability, while minimizing the possibility of damage of breakage of glass tubes or gas chambers typically associated with prior art devices. Fewer calibration operations and fewer repairs are also attendant the construction. Finally, because of its compact size, solid state stage construction and use of relatively low cost components, the detector can be manufactured at lower cost than present generation thickness measurement systems.

Because of its low cost and compact construction, a plurality of measuring devices can be arrayed across an extruded film to measure the material thickness simultaneously across its width at discrete points. Because of the complexity and size of present generation equipment, this approach cannot now be achieved, and instead mechanical scanning of a thickness measuring device across the width of a sheet must be employed which has undesired complexity due to the mechanical scanning mechanism. Each of the plurality of thickness measuring devices provided in the array can then be used to control a respective section of processing machinery such as respective lip sections of an extrusion die to control the extruded product to desired specifications.

The above and other objects, advantages and features of the invention will be more readily understood from the following detailed description of the invention which is provided in connection with the accompanying drawings.

DETAILED DESCRIPTION OF THE INVENTION

Figure 1:
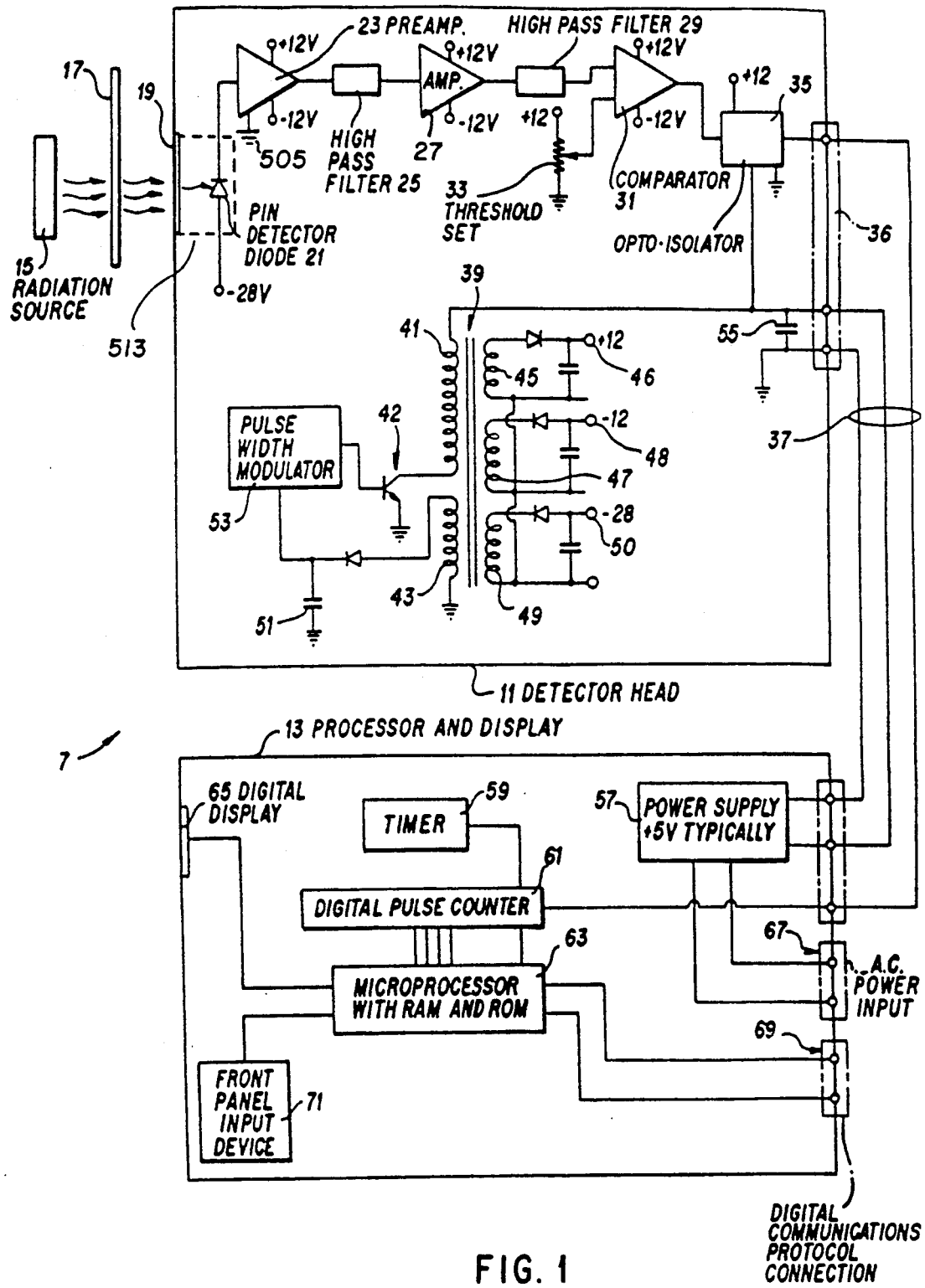
FIG. 1 illustrates in electrical block and schematic form a first embodiment of the present invention.

FIG. 1 illustrates the thickness/density measuring system of the invention in partly schematic, partly block diagram form. The thickness/density measuring system 7 is constructed in two component parts identified in FIG. 1 as detector head section 11 and processor and display section 13. These sections are interconnected by a low-voltage cable 37 and are described more fully below.

Detection head section 11 includes the detecting electronics for a thickness/density measurement, while processor and display section 13 contains the processing and display components for providing a digital display of a thickness/density measurement and/or an output signal representative of the thickness/density measurement which can be used for control purposes.

Turning now to the detector head section 11, it includes a window 19 in the housing which blocks entry of light radiation into the housing, but which permits particle radiation to pass therethrough. Suitable materials which can be used for window 19 include aluminized mylar. Disposed behind window 19 and within housing 11 is a PIN diode 21 which is sensitive to radiation, both light radiation and particle radiation. As noted, window 19 is impervious to light radiation so that PIN detector 21 can only detect particle radiation such as X-rays, beta rays and gamma rays. This particle radiation is emitted by a radiation source 15 which is spaced from window 19. The material 17 to be measured is placed between the radiation source 15 and window 19.

The output of PIN diode 21 is connected to a charge sensitive preamplifier 23 the output of which is connected to a first high pass filter 25. The output of the high pass filter 25 is in turn passed to the input of a low noise operational amplifier 27, the output of which then passes through a second high pass filter 29. The output of the high pass filter 29 represents voltage pulses which correspond to charges which are detected by the PIN diode 21. The output of the high pass filter 29 is connected to the input of a comparator 31 which has a threshold set by resistive network 33 applied to another input thereof. The high pass filters block low frequency noise components while the threshold of comparator 31 is set so that miscellaneous noise which does not constitute a valid detection pulse will not affect the readings of the instrument. When the output of the high pass filter 29 exceeds the set threshold the comparator 31 provides an output pulse which is then fed to an opto-isolation and line driver circuit 35. The output of the isolation circuit 35 is then connected to a terminal strip on the detector head section 11 for connection with additional processing electronics in the digital processing and display section 13.

Before describing the digital processing and display section 13, the remainder of the circuitry provided in the detector head section 11 will be described. In order to provide operative power to the various electronic components within the detector head section 11, a power supply is built therein. Because the PIN diode requires different voltages than other electronic components within the detector head assembly, a multivoltage power supply is provided in the form of a transformer 39 having a plurality of primary windings 41 and 43 and a plurality of secondary windings 45, 47 and 49. The secondary windings are connected to respective diode/capacitor networks and provide the operating D.C. voltages required for the various circuit components within the detector head section 11. One side of primary winding 41 is connected to receive an unregulated input voltage applied to an input terminal strip 36 at the detector head section 11 and received from the digital processing and display section 13. This unregulated voltage supply is switched by a transistor switching device 42 under control of a pulse width modulator 53. Pulse width modulator 53 also receives a D.C. voltage input from a primary reference winding 43 through a diode capacitor network such that the pulse width modulator 53, network 51 and switching device 42 as well as the primary winding connections function to provide a regulated voltage output at the secondary terminals 46, 48 and 50.

An important aspect of the present invention is that the detector head section 11 can be made of very small size and the power supply for the detector head operates on low D.C. voltages, typically less than ±30 volts, which makes the detector head suitable for placement in many environments wherein high voltages and/or bulky and complex equipment cannot be provided.

The digital processing and display section 13 provides a low voltage power supply input to the detector head 11 and supplies this via a power supply circuit 57 which receives an A.C. power input 67. Alternatively, a D.C. power source can be provided. The digital processing and display section 13 further includes a timer 59 which defines time windows during which a digital pulse counter 61 is enabled to count pulses which are received from the output of the opto-isolation circuit 35 in the detector head section 11. The pulse counter 61 is gated by the timer 59 to establish a pulse rate counting circuit which provides a count pulse for a given period of time. The output of the digital pulse counter 61 is in turn gated into a microprocessor 63 which includes the usual ROM and RAM memory circuits for storing programs and data. A manually operable panel input service 71, containing a plurality of input switches or keys and input setting devices, is also provided for providing input information to the microprocessor 63. The microprocessor also provides as output signals a digital signal on terminals 69 representing a thickness or density measurement and an output signal to a digital display 65 provided within the digital processing and display section 13 also representing a thickness or density measurement.

By separating the detector head 11 from the processor and display 13, the size of the detector head can be reduced considerably as discussed above. Furthermore, if desired, a plurality of detector heads 11 could be multiplexed to a common processor and display 13 to further reduce costs.

At this point it should be noted that the first embodiment of the invention can be used for either a thickness or density measurement or a denier measurement, depending on the programming of microprocessor 63 as will be more fully described below.

Microprocessor 63 contains an algorithm for calculating a thickness, density or denier measurement based on the count rate it receives from the digital pulse counter 61. It is first necessary to calibrate microprocessor 63 with reference data corresponding to a known thickness, density or denier and a measured count rate for that known thickness, density or denier so that later measurements can be related to this calibration standard. The calibration for and measurement of an unknown thickness of a film will first be described.

Figure 2:
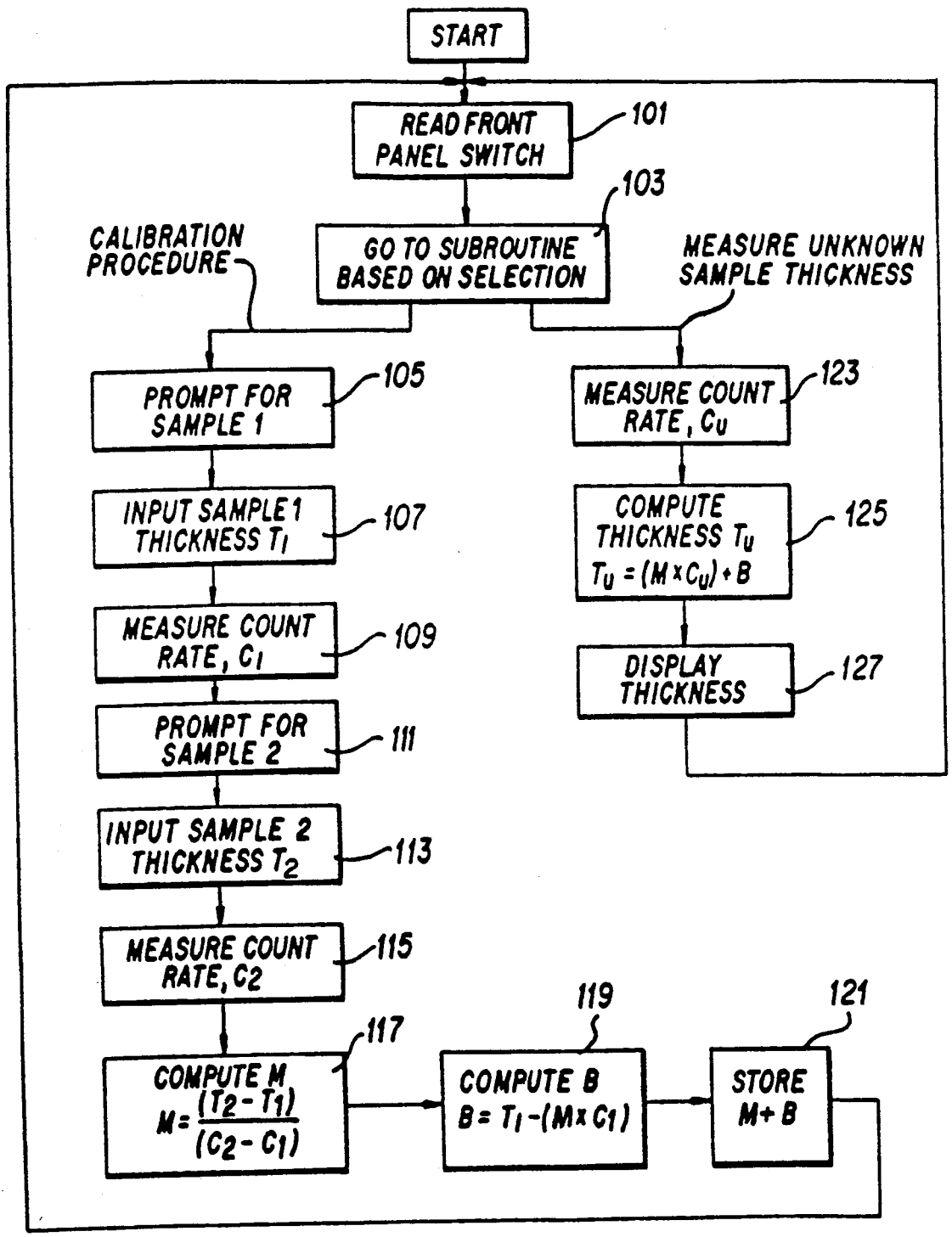
FIG. 2 illustrates in flow chart form a microprocessor program for a method of calibrating and measuring an unknown thickness using the embodiment shown in FIG. 1.

FIG. 2 illustrates in flow chart form the programming of microprocessor 63 which enables it both to be calibrated in the first instance and then to take thickness measurements thereafter. The operation depicted in FIG. 2 is based on a two sample calibration technique. In a first step 101 of the processing, a switch on the front panel input device 71 of FIG. 1 is read to determine whether a calibration or a measuring operation is desired. In step 103 the microprocessor determines which type of processing is required. If a calibration procedure is selected by the front panel input devices 71, the microprocessor proceeds to step 105 where it displays on the digital display 65 a prompt to an operator instructing him to insert a reference sample into the measuring path between source 15 and window 19. In addition, the microprocessor further reads a thickness setting input device, e.g., digital value switches, on the front panel input device 71 to obtain a signal representing an actual thickness $T_1$ of this sample. Following step 107 the microprocessor proceeds to step 109 where it measures the count rate $C_1$, for the sample of known thickness in step 109. Following this the microprocessor activates the digital display 65 to prompt an operator to place a second sample of known thickness between the radiation source 15 and window 19. In addition, the microprocessor receives an input on front panel input device 71 an entered thickness $T_2$ corresponding to the second sample. Thereafter, the microprocessor proceeds to step 115 and measures the count rate $C_2$ for the second sample and after this proceeds to step 117 where it computes a slope M value using the equation:

$$M = (T_2 - T_1)/(C_2 - C_1) \qquad (1)$$

Following this, the microprocessor proceeds to step 119 where it calculates an intercept value B as $$B = T_1 - (M \times C_1) \qquad (2)$$

The slope value M and intercept value B are then stored in step 121 for later use by the instrument in calculating thickness of a sample of unknown thickness.

Returning to step 103, if an actual measurement is desired, the microprocessor proceeds from step 103 to 123 where it measures a count $Cu$ rate for a sample of unknown thickness. Thereafter it computes an actual thickness $T_u$ using the equation $$T_u = (M \times Cu) + B \qquad (3)$$

where M and B are the values previously obtained in the calibration step. This yields a thickness measurement which is then displayed on digital display 65 in step 127 or alternatively output to control equipment on lines 69 of the digital processing and display unit 13.

Figure 3:
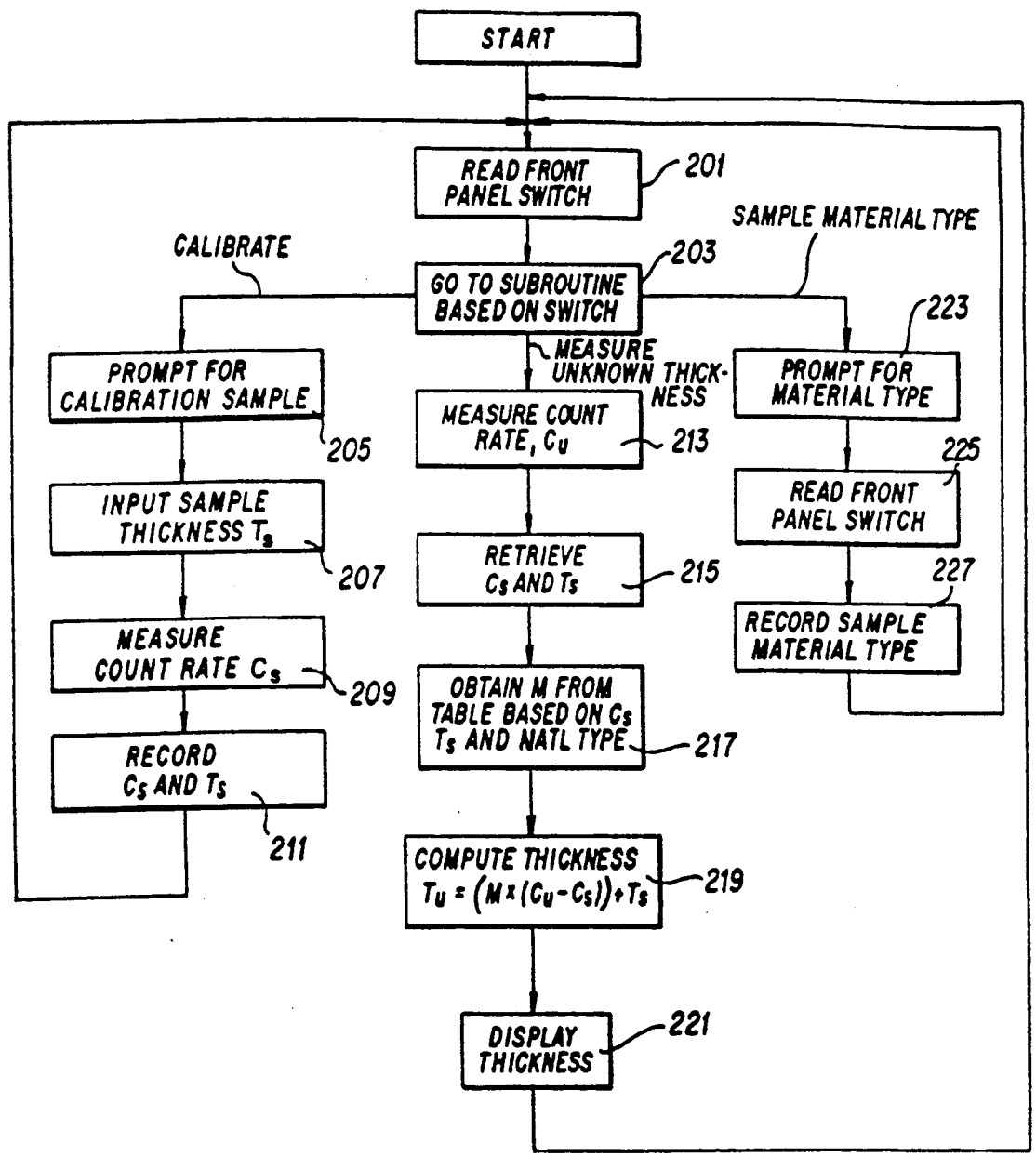
FIG. 3 illustrates in flow chart form a microprocessor program for another method of calibrating and measuring an unknown thickness.

FIG. 3 shows an alternate thickness calibration and measurement program which can be used with the microprocessor 63. In this processing sequence, a single calibration sample is used to calibrate the instrument. In a first step 201 the front panel input device 71 is read to determine whether a calibration, a measurement, or a material type entry routine is to be executed. If the front panel switch at input device 71 indicates a calibration routine is desired, step 203 causes retrieval and execution of the calibration subroutine. The microprocessor thus proceeds to step 205 where it prompts an operator on the digital display 65 to insert a calibration sample between the radiation source 15 and the window 19. In addition, a thickness $T_s$ of the material sample is input at step 207 on the front panel input device 71 and following this step the microprocessor proceeds to step 209 where it measures a count rate $C_s$. It then records the measured count rate $C_s$ and the inserted sample thickness $T_s$ in step 211 and proceeds back to step 201. With the FIG. 3 calibration technique, a material type entry, e.g., polyester, nylon, acrylic, etc. must also be made at input device 71. When the material type entry is indicated on the front panel input device 71, the microprocessor 63 senses this in step 203 and then branches to step 223 where it displays a prompt on the digital display 65 for an operator to enter, via the front panel input device 71, a material type which is used in the calibration. Material type as set in the front panel input device 71 is then read by the microprocessor 63 in step 225 recorded and stored in step 227. All the data required for the microprocessor now to calibrate itself for making an actual measurement of the material thickness is present. Thus, when the front panel input device 71 is now set for a measurement, step 203 executed by the microprocessor will cause a measurement routine to be started at step 213 where the count rate $C_u$ of an unknown sample placed between the source 15 and window 19 is taken. After this, in step 215, the values $C_s$ and $T_s$ obtained during the calibration routine are retrieved following which, in step 217, an M value is obtained based on a table stored in the microprocessor interrelating the count values $C_s$, the set thickness $T_s$ and the inserted material type. This table is a stored lookup table and contains various values of M based on various combinations of values of $C_s$, $T_s$ and material type. Following step 217, where the value M is obtained from the lookup, a thickness computation is made in step 219 based on the formula $$T_u = (M \times (C_u - C_s)) + T_s \qquad (4)$$

The thickness value is then displayed in step 221 on display 65 or output on lines 69 to further processing or control apparatus, following which the microprocessor proceeds back to the beginning of the program.

The calibration techniques described in FIGS. 2 and 3 have their respective advantages and disadvantages. The calibration technique of FIG. 2 is straightforward and requires only operator entry of known thickness values, but requires two samples of different known thicknesses for calibration. While it provides a very good calibration of the instrument, the requirement of having two samples of close, but measurably different thickness, may be difficult at times and sometimes even impossible to achieve. Consequently, the FIG. 3 calibration technique, which is somewhat more cumbersome to execute, requires only one sample, has that as one benefit. The theory on which the calibration of FIG. 3 is based is that a particular count rate observed under any given circumstances will be effected by a number of factors including source strength, source to detector separation and geometry, losses in the detector window, dirt accumulation on the detector window, electronic sensitivity and threshold setting, and, of course, material composition and thickness. A single calibration sample observation will establish the net result of the combination of these parameters at a particular point in time. In production use, the only variable of practical concern is the unknown material thickness for a reasonable period of time. A reasonable period of time is established by such factors as a half-life of a radioactive source which typically would be quite long compared to a production period, the drift rate of the electronics, and the rate of accumulation of dirt on the window. The FIG. 3 calibration technique is based on the fact that once a count rate has been established for a given thickness of a type of material under a certain condition of source strength, source to detector separation etc., the variation and count rate with material thickness represented by M in Equation 4 above, can be predetermined and stored permanently in the device for use during production measurements. Since M will be somewhat dependent on the nominal count rate and type of material being measured, a number of values of M can be predetermined and stored in the microprocessor 63 and an M can be selected by microprocessor 63 which most closely matches the operating conditions. The material type is thus operator selectable though the front panel input device 71 and the nominal count rate can be taken during a calibration sample count so that the microprocessor 63 can then make appropriate selection of the value M. To determine the initial values of M which can be permanently stored in the microprocessor 63 repeated application of Equation 1 above can be used over a range of material types and thicknesses. These results can be arranged in a tabular form so that when a particular calibration sample thickness and material type are entered and the count rate observed, the value of M which most closely matches these conditions can be selected for use.

In summary, the calibration technique illustrated in FIG. 3 has the advantage that a single sample of production material, manually measured for thickness, can be used as the calibration sample and to establish the nominal count rate of production for the algorithm to select a proper value of M for later thickness measurements. A single step calibration procedure is thus provided which is more readily used by unskilled operators.

Figure 4:
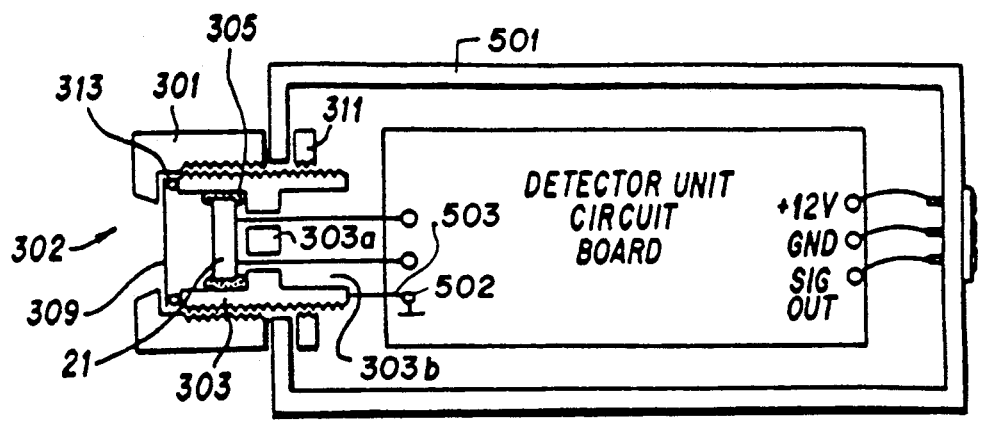
FIG. 4 illustrates a modification of the FIG. 1 embodiment showing a different way of mounting a particle radiation detector.

FIG. 4 illustrates a modification of the detector head 11 illustrated in FIG. 1. In this embodiment, an easily removable detector head assembly is provided which can be readily fixed to production machinery. The PIN diode 21 is shown bonded by an Epoxy 305 or similar adhesive to the inner periphery of an exteriorly threaded conductive sleeve 303. An aluminized mylar entrance window in the form of a film 309 is provided at one end of the threaded sleeve 303 with an O-ring seal 313 being provided between the mylar window and an end of threaded sleeve 303. A conductive locking cap 301 is threaded onto the outer periphery of threaded sleeve 303 which serves to hold the mylar film 309 in place and which also serves to provide a backstop which limits the amount of travel of the threaded sleeve into an opening in the section 11. The conductive (aluminized) layer of the mylar film 309 is electrically connected to locking cap 301, as by being pressed thereagainst. In this instance the aluminized layer of film 309 faces outwardly of the detector head assembly. Cap 301 includes an opening 302 at a front side thereof at a position corresponding to the location of the mylar window 309. A conductive backing nut 311 is screwed onto the threaded shaft 303 behind a wall of the detector head housing 11 to hold the entire detector head in place. The leads of the PIN diode 21 pass through at least one hole contained in a plate-like back wall 303$a$ of an internal bore 303$b$ of threaded sleeve 303. The leads are insulated and therefore do not electrically connect with back wall 303$a$. The PIN diode leads are then affixed to an electronic circuit board containing the remainder of the electronics of the detector head assembly shown in FIG. 1. The conductive backing nut 311 fixes the assembly of locking cap 301, and threaded shaft 303 to a body 501 which is preferably conductive. Body 501, backing nut 311, locking cap 301 and threaded shaft 303 all form part of a housing for the PIN diode 21 and the detector unit circuit board. The arrangement of the mylar film 309, conductive threaded sleeve 303 including back wall 303a, and conductive cap 301 provides a conductive shield which entirely surrounds the PIN diode 21. This shield is preferably grounded to a ground point 502 for the circuitry contained within detector head 11, and is most preferably connected to the ground point 505 of charge sensitive preamplifier 23 (FIG. 1). FIG. 4 illustrates one such grounding by an electrical connection 503 provided between threaded sleeve 303 and a ground terminal 502 on the detector unit circuit board. This ground terminal is preferably also the ground conductor 505 for preamplifier 23. Body 501 can be conductive and if it is and it is also grounded to the detector unit circuit board so that an electrical conductive shield is also provided around the entirety of detector unit circuitry. If body 501 is conductive and grounded, to the ground point for sleeve 303, the back wall 303a of threaded sleeve 303 may be omitted, although it is preferably retained to enable electrical shielding for the PIN diode by itself.

The PIN diode shielding described above with respect to FIG. 4 can also be applied to an arrangement of the type shown in FIG. 1 as illustrated by the dotted lines denoting at shielding 513 around PIN diode 21 in FIG. 1. Alternately, the shielding of the PIN diode 21 can be done by making the entire housing of detector head 11 of a conductive material and placing the conductive layer of window 19, preferably of aluminized mylar, against and to surround a hole in the housing to electrically connect the aluminized layer with the conductive housing.

The design of the housing illustrated in FIG. 4 is particularly advantageous as it allows ready replacement of the actual detector head itself, including the PIN diode, without requiring a complete disassembly of the components within housing 13.

The aluminized mylar window 19 and film 309 illustrated in FIGS. 1 and 4 can be formed of a mylar film having a thickness of 0.5 to 5.0 mils. In some applications it may be desirable to use an even thinner window to minimize the absorption or scattering of radiation by the window. In this case a thickness range of 0.1 to 5.0 mils would be appropriate. Each of window 19 and film 309 can also be made of other conductive materials such as a thin aluminum or a stainless steel foil. In addition, the PIN diode illustrated in FIGS. 1 and 4 is of a windowless construction wherein protective layers covering the active PIN areas are not provided by the manufacturer to maximize radiation sensitivity. Thus the mylar window 19 or film 309 provides the principal form of protection for PIN diode 21. Mylar film 309 of FIG. 4 contains the same aluminized film construction as FIG. 1 which blocks light radiation from striking the PIN diode 21, thereby improving reliability of detection of particle radiation.

Figure 5:
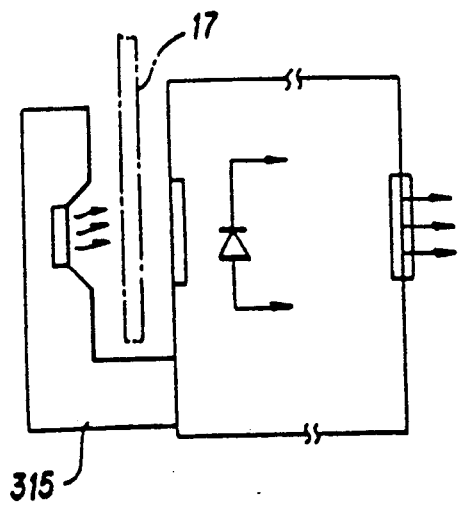
FIG. 5 illustrates another modification of the FIG. 1 embodiment.
Figure 6:
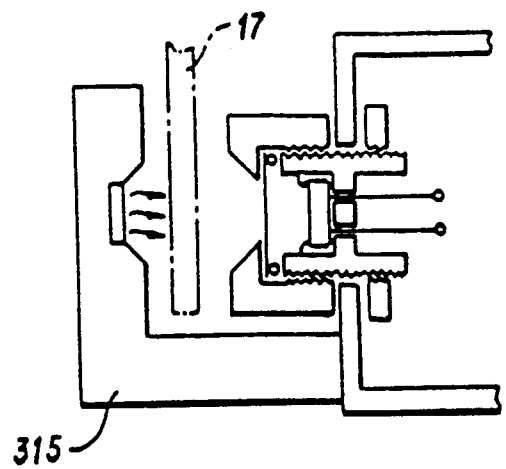
FIG. 6 illustrates a modification of the FIG. 4 embodiment.

In the embodiments of the invention thus described, the radiation source, which may emit gamma rays, X-rays, or beta rays, is fixedly spaced from the detector head section 11 by being mounted on a separate support. It is also possible to provide an integral support on the detector head section 11 for the detector source which would then provide a fixed gap between the source and PIN detector within which a material whose thickness is to be measured can be placed. This embodiment is illustrated in greater detail in FIGS. 5 and 6 which respectively correspond to the embodiments of FIGS. 1 and 4, but with an extension arm 315 integrally connected to section 11 and extending therefrom in an L-shape fashion to provide a gap between the radiation source and radiation detector. With this integral construction, it is possible to construct the entire detector unit as a simple portable assembly. Moreover, since the detector unit operates on low voltages, it is further possible to incorporate all of the electronics including those of the digital processing and display unit provided in section 13 of FIG. 1 into a single housing which is readily portable to different environments of use.

Figure 7:
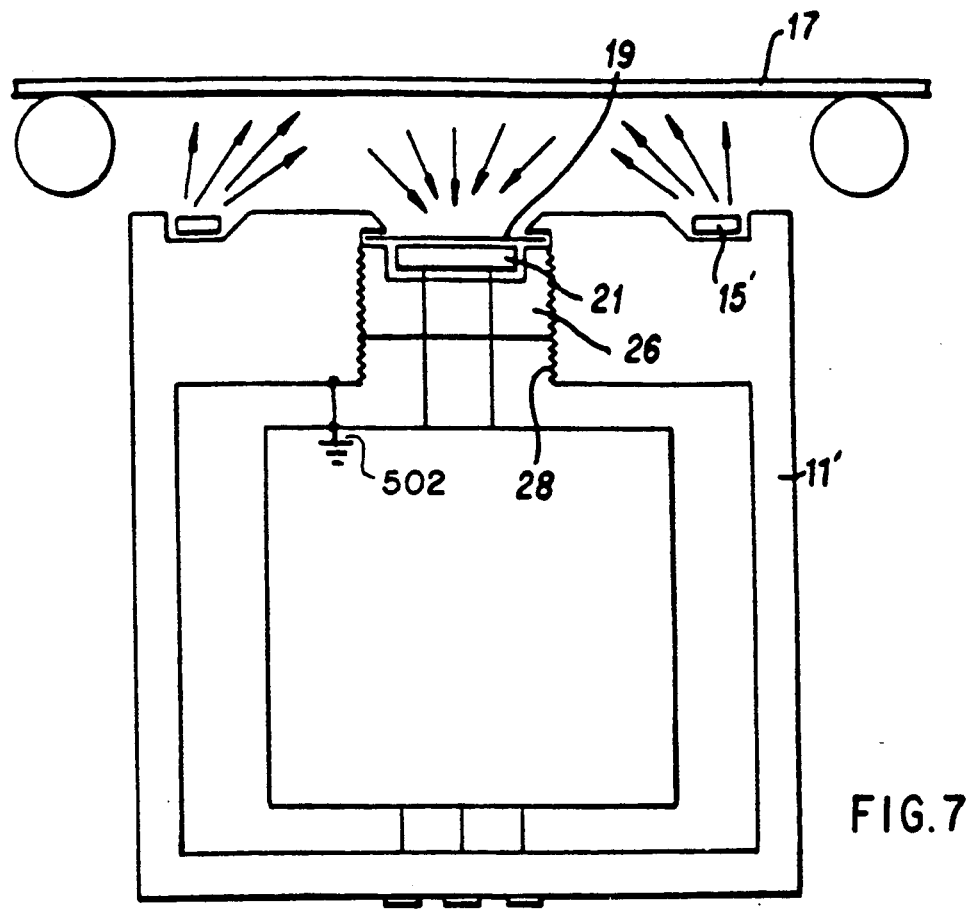
FIG. 7 illustrates another modification of the FIG. 1 embodiment using a back-scatter radiation technique.

FIG. 7 illustrates a modification of the invention wherein the detector head section 11 is used in a backscatter radiation detection technique. In this embodiment, the PIN diode 21 is mounted within a relatively thick material portion of one end of the section 11. In addition, the radiation source 15' is also mounted in the same end of the housing but the housing is configured so that most, if not all, of the radiation from source 15 projects outwardly of the housing and not directly toward the PIN diode 21. As a consequence, a material can be stretched across the one end of the section 11 in front of the radiation source 15 and PIN diode 21, and backscatter radiation can be detected from the source by the PIN diode. The amount of backscattering which occurs will be dependent on material thickness and thus the instrument can be calibrated for radiation count based on backscatter using either of the calibration techniques described above with respect to FIGS. 2 and 3. In the FIG. 7 embodiment, the PIN diode is mounted in a conductive PIN diode holder 26 which has external conductive screw threads which screw with a conductive threaded bore 28 provided in one end of the detector head section 11 which is formed of conductive material. The window 19 has a conductive surface which engages with the conductive head section 11 so that the PIN diode is, once again, entirely surrounded by a conductor for shielding. The leads of the PIN diode pass through bores provided in holder 26 and are attached to a circuit board containing the detector head electronics. The shielding around the PIN diode is grounded to this circuit board and is preferably grounded to a ground terminal 505 of the charge sensitive preamplifier 23.

The only difference between the microprocessor 63 programming for calculating a thickness value when the backscatter approach is used is that the numerical sign of the slope constant M will evaluate to be positive when the calibration procedure is followed. This is due to the fact that the count rate increases for increasing material thickness in the backscatter mode while it decreases for increasing material thickness in a transmission mode.

Figure 8:
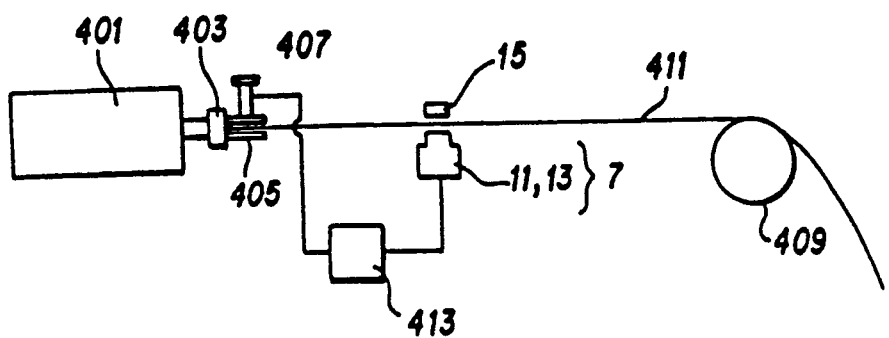
FIG. 8 illustrates a control system for an extrusion die utilizing the present invention.
Figure 9:
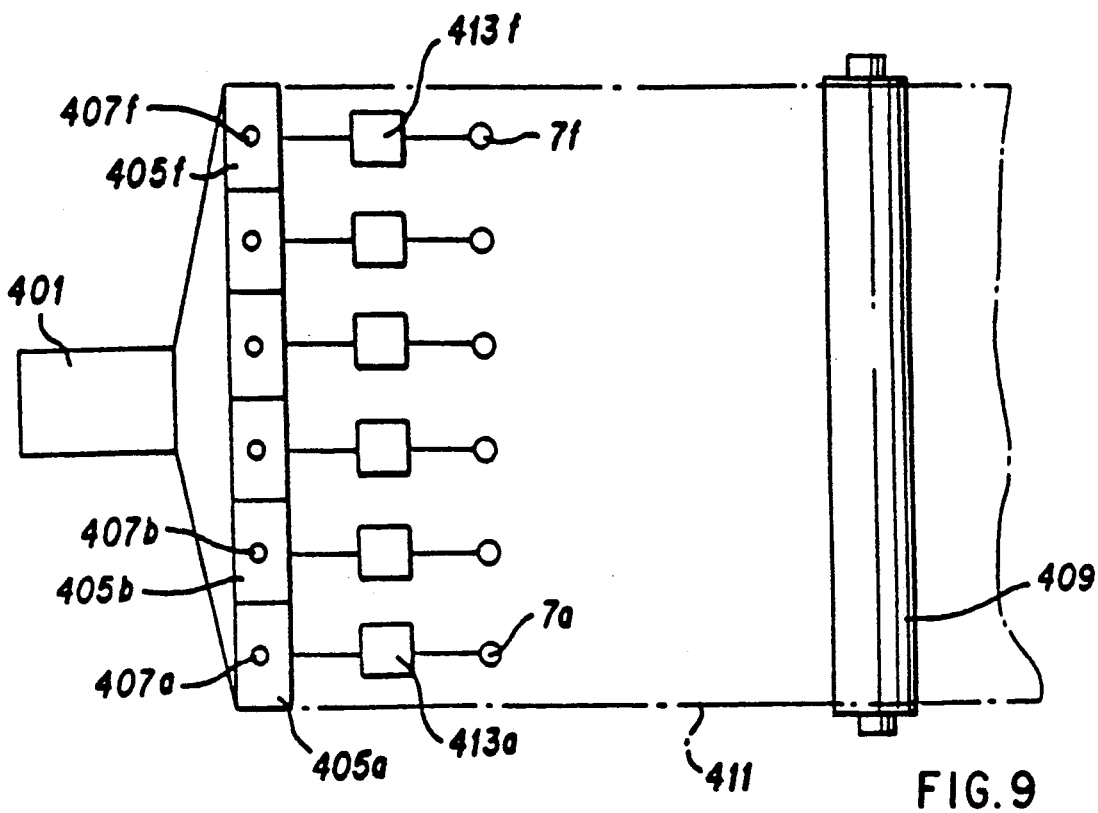
FIG. 9 illustrates an array of thickness measuring detectors for use in a control system for controlling the thickness of an extruded film.

FIGS. 8 and 9 illustrate a control system with which the thickness measuring device 7 of the invention can be particularly suitably employed. The control system is used to control sections of die lips of a film extrusion system. FIG. 8 is a side view of the system which includes an extruder barrel 401 supplying a plasticized material to a die 403 for extruding a thin sheet of plastic material. Die 403 includes die lips 405 at the outlet end thereof which are adjustable with respect to the gap defined by the lips to thereby adjust the thickness of the material leaving the die. Typically, a bolt 407 is used to adjust the die lips with manual operation of the bolt being used to effect a course adjustment and with a system providing a fine adjustment of the gap between the die lips. In many instances, the fine adjustment is provided by actually heating the bolt 407 to provide fine adjustment of the die gap. This heating is controlled by a control system 413 which includes a typical PID (proportional, integral, derivative) controller which in turn is connected to the output of the thickness measuring device 7 illustrated in FIG. 1, particularly to the output provided at terminals 69. Film 411 which passes from the die lips is taken over a haul-off roller 409. In order to measure thickness, a radiation source 15 is provided on one side of the film and the detector, including housing sections 11 and 13 are provided on the other side of the film. Alternatively, a backscatter technique may be employed as illustrated in FIG. 7. In either event, the output signal of the thickness measuring device is applied to the PID controller 413 to in turn control the heating of bolt 407 which finely controls the gap of die lips 405. As illustrated in FIG. 9, for a sheet of substantial width, the die lips 405 are divided into a plurality of die lip sections 405a...405f, with each being controlled by respective die bolts 407a...407f and with the heating of each die bolt being in turn controlled by a respective PID controller 413a...413f. The inputs to each of these controllers are respectively derived from individual thickness measuring devices 7a..7f constructed as described above. With this arrangement, each measuring device 7 measures a portion of the width-wise extent of the film 411 and in turn controls individually its own heater bolt 407 so that the thickness of each section of the width-wise dimension of the film is individually and separately controlled.

Thus far, the invention has principally been described with reference to thickness measurements. However, it is also possible to use the same apparatus for measuring density. To allow density measurement, three conditions must occur, the thickness of a material placed between the source and detector must remain constant, or the material completely fills the volume between the source and detector as in a fluid medium, or the thickness is known and fed into an algorithm by an external thickness measuring device which can then calculate a density from the measured thickness and known material characteristics.

Figure 10:
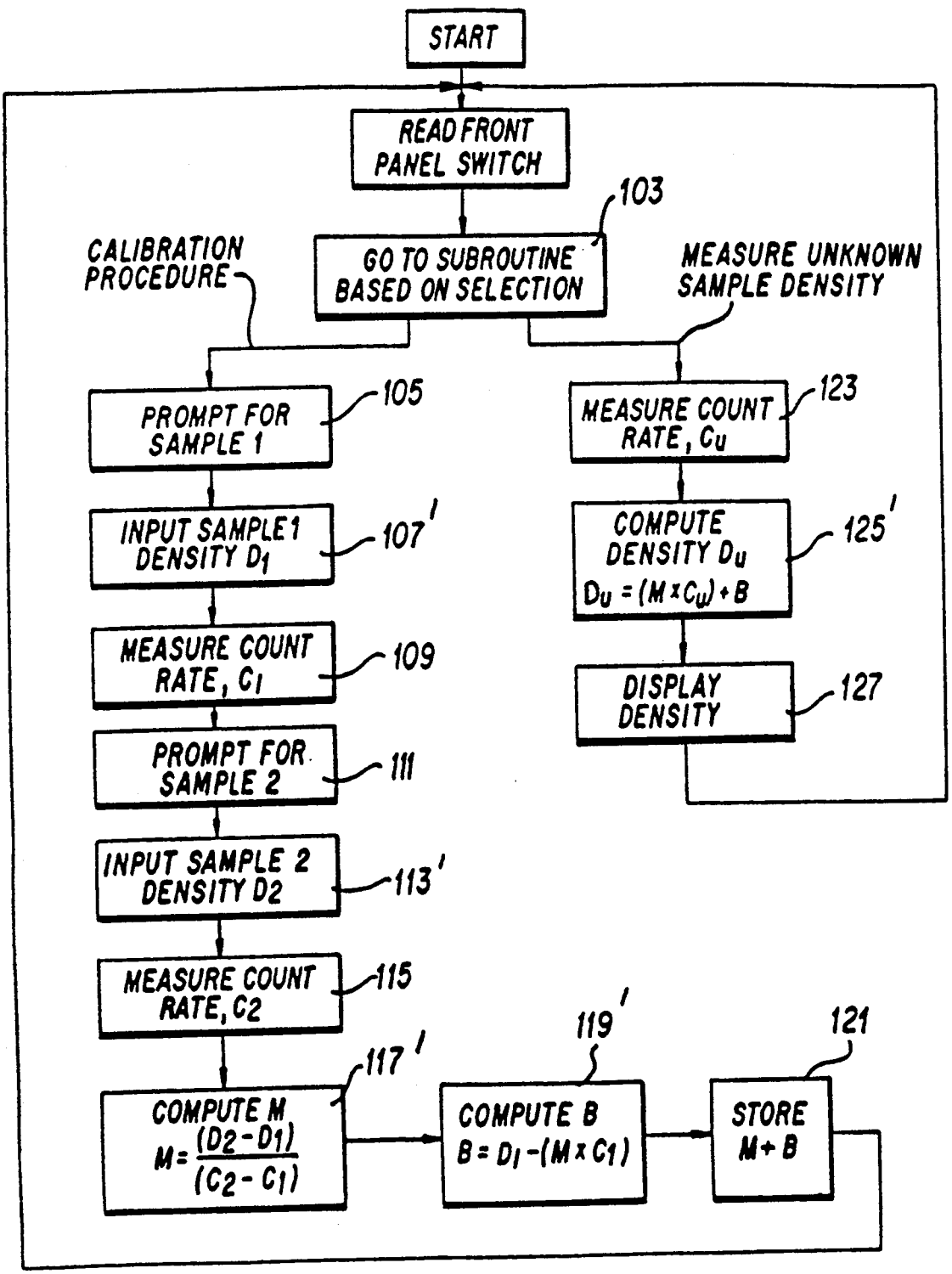
FIG. 10 illustrates in flow chart form a microprocessor program for a method of calibrating and measuring an unknown density using the embodiment shown in FIG. 1.

FIG. 10 shows a modification of the FIG. 2 flow chart to permit use of the FIG. 1 apparatus for a density measurement. As shown therein, step 107 is modified as new step 107', step 113 is modified as new step 113', and steps 117, 119 and 125 are all modified as new steps 117', 119' and 125'.

Without describing again all of the steps illustrated in FIG. 2 which are common in FIG. 10, those steps which are common have the same reference numbers. Those steps which are changed are designated by a prime (') symbol. In step 107' of FIG. 10, a density $D_1$ is entered for a first material sample while in step 113' a density $D_2$ is entered for a second material sample. In step 117', the slope M is computed using the formula $$M = (D_2 - D_1)/(C_2 - C_1) \quad (5)$$

In step 119', the intercept is computed as $$B = D_1 - (M \times C_1) \quad (6)$$

With the now stored calibration values of M and B, a density measurement can then be carried out, with the density computation made in step 125' as $$D_u = (M \times C_u) + B \quad (7)$$

Figure 11:
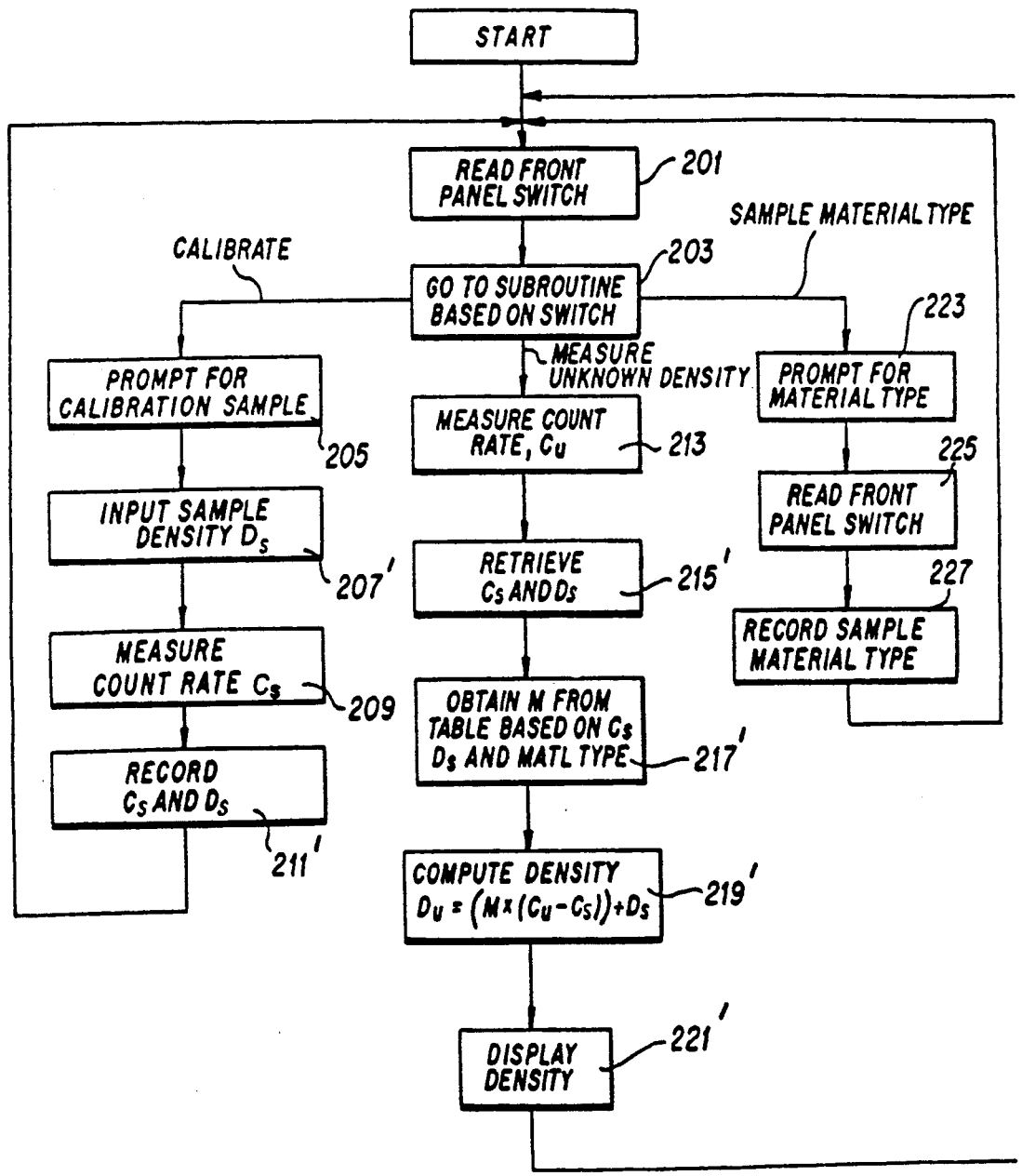
FIG. 11 illustrates in flow chart form a microprocessor program for another method of calibrating and measuring an unknown density.

FIG. 11 illustrates the modifications needed for the FIG. 3 flow chart to attain a density measurement.

In the calibration technique for density measurement illustrated in FIG. 11, an input sample density is input to the system in step 207' and this together with a detected count rate $C_s$ for the sample is recorded at step 211'. A sample material type is also entered and stored at step 227. Finally, to calculate a density measurement, a measured count rate $C_u$ at step 213 is first taken following which values $C_s$ and $D_s$ entered during the calibration sequence are used to obtain a slope value M from a table based on $C_s$, $D_s$ and material type. From this, a density measurement can then be calculated using subroutine represented by steps 213, 215, 217', 219', and 221' as follows. A count rate is measured at step 213 following which the value $C_s$ and $D_s$ are retrieved in step 215'. From this the value of M is obtained from a stored table based on the values of $C_s$, $D_s$ and material type. In step 219' the density $D_u$ is computed from the formula $$D_u = (M \times (C_u - C_s)) + D_s \quad (8)$$

The density value is then displayed on digital display 65 or sent to output terminals 69 in step 221'.

It is also possible to calculate a density when a thickness of a sample is known or measured from the equation $$D_u = T_s/T_u \times ((M(C_u - C_s)) + D_s) \quad (9)$$

where $D_s$ is a density of a calibration sample, M is the slope factor calculated in the manner described in steps 213...221' of FIG. 11, $T_u$ is a thickness of a sample in front of the detector and $T_s$ is a thickness of density standard.

It is also noted that the apparatus of the invention can also be used as a material flaw or void detection apparatus since flaws and voids can be recognized by a change in a density value.

As is apparent from the foregoing description, the present invention provides a compact thickness/density measuring apparatus which can be used in a wide range of environments, particularly environments where high voltages and/or complex and bulky structures cannot be used. The measurement instrument is compact and easily transportable and can be configured as a portable unit.

Thus far, a description has been provided of embodiments of the invention for measuring thickness or density of an object or material. The invention may also be used to measure the thickness of a coating on a substrate.

In coating applications it is often desired to measure the thickness of a coating layer applied to a substrate, for example, to ensure coating uniformity. Often the density of the coating material is different from the density of the substrate material so that one cannot simply use two thickness measuring systems as described above, one upstream of the point of application of the coating, and the other downstream thereof, to develop a subtraction signal representing coating thickness (i.e., downstream material thickness—upstream material thickness=coating thickness). The differing material densities will give an erroneous measurement. In such a coating system both the substrate material and the coating material have variable thicknesses which are desired to be known.

Figure 12:
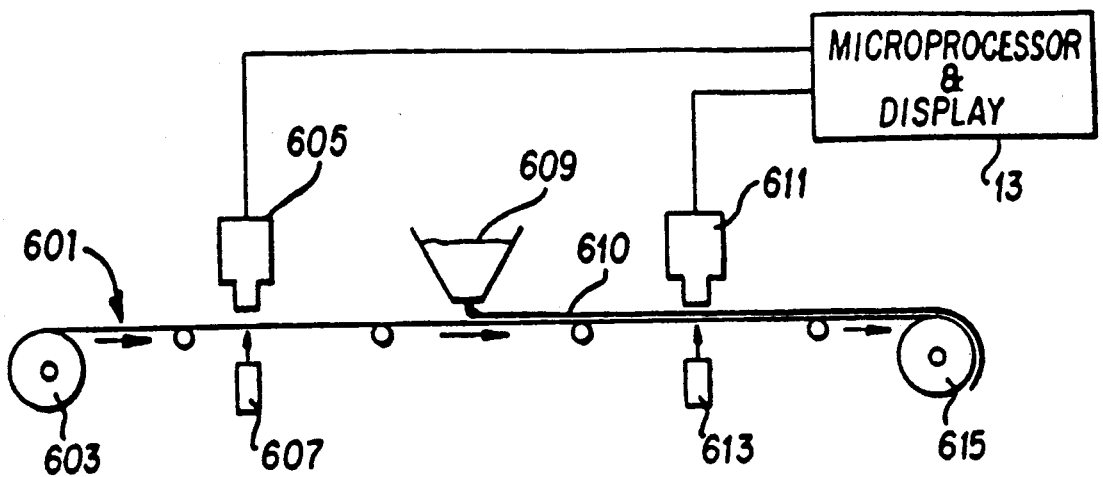
FIG. 12 illustrates a system employing two thickness detectors for measuring the thickness of a coating applied to a base layer or substrate.
Figure 13:
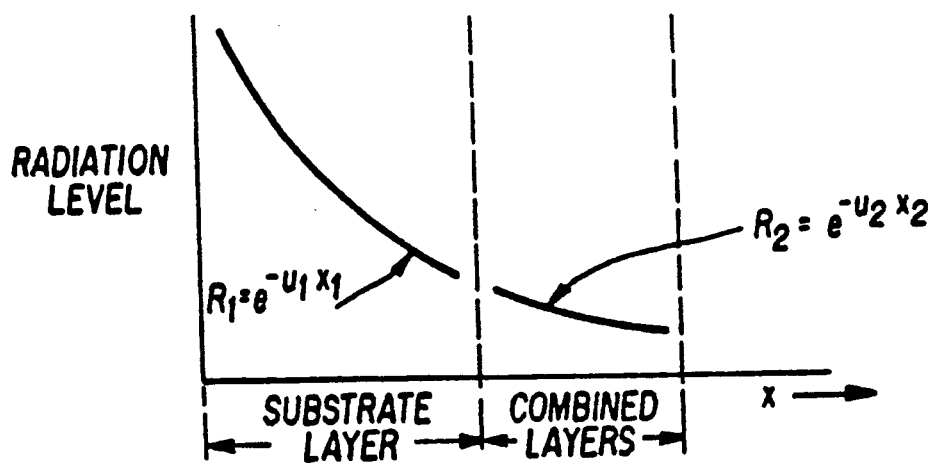
FIG. 13 is a graph useful in the explanation of the operation of the FIG. 12 system.

FIGS. 12 and 13 illustrate an embodiment of the invention for accurately determining a coating thickness using a particle radiation detection system of the type illustrated in FIG. 1.

In FIG. 12 a substrate or backing material layer 601 is taken from a supply roll 603 and gasses a first particle radiation thickness detector 605 which detects particle radiation passing through substrate 601 from radiation source 607. After passing detector 605, the substrate layer 601 passes coating applicator 609 which applies a coating layer 610 to the substrate layer 601. The coating applicator 609 may take any of the known forms such as a nozzle, roller, blade, etc. It may even take the form of a laminator which laminates a material layer 610 to substrate 601. Downstream of the coating applicator 609 is a second particle radiation thickness detector 611 which detects radiation passing through both layers 601, 610 from a radiation source 613.

Because of the non-linear effects of absorption of the radiation in materials of different densities, a thickness output of radiation detector 605 cannot be simply subtracted from a thickness output of radiation detector 611 to provide a thickness value corresponding to the thickness of coating layer 610. The radiation attenuation of the coating 610 is different and typically less than that of the substrate 601. FIG. 13 illustrates the exponential attenuation profiles of radiation through the substrate layer 601 and through the combined layers 601 and 610.

The exponential attenuation law $R = e^{-ux}$ holds separately for each layer where R is the relative radiation intensity, u the attenuation coefficient of each layer and x the distance a radiation beam passes into the material.

If the detector 605 is located close to detector 611 so that the same substrate thickness is detected by both detector 605 is stored and forwarded to detector 611, the coating thickness can be found as follows.

The radiation level seen by detector 605 is given by $$R_s = e^{-u_s x_s} \quad (10)$$

where $u_s$ is the attenuation constant of the substrate and $x_s$ is the thickness of the substrate. The radiation level seen by detector 611 has a further reduction of radiation due to the different attenuation constant of the coating layer 610. It is given by:

$$R_c = e^{-u_s x_s} e^{-u_c x_c} \quad (11)$$

where $R_c$ is the radiation level measured by detector 611, $u_c$ and $x_c$ are the attenuation constant and thickness of the coating respectively. The attenuation constant $u_c$ can be measured or is known for the particular material used for coating layer 610. What needs to be determined is $x_c$, the thickness of the coating layer 610. Substituting equation 10 into equation 11 yields:

$$R_c = R_s e^{-u_c x_c} \quad (12)$$

taking the logarithm, $$ln(R_c/R_s) = -u_c x_c \quad (13)$$

which gives:

$$x_c = -1/u_c \, ln \, (R_c/R_s) \quad (14)$$

Since $R_s$ is the detected count rate for detector 605, $u_c$ is known, and $R_c$ is the detected count rate for detector 611, equation 14 can be solved to yield a coating thickness $x_c$.

Figure 14:
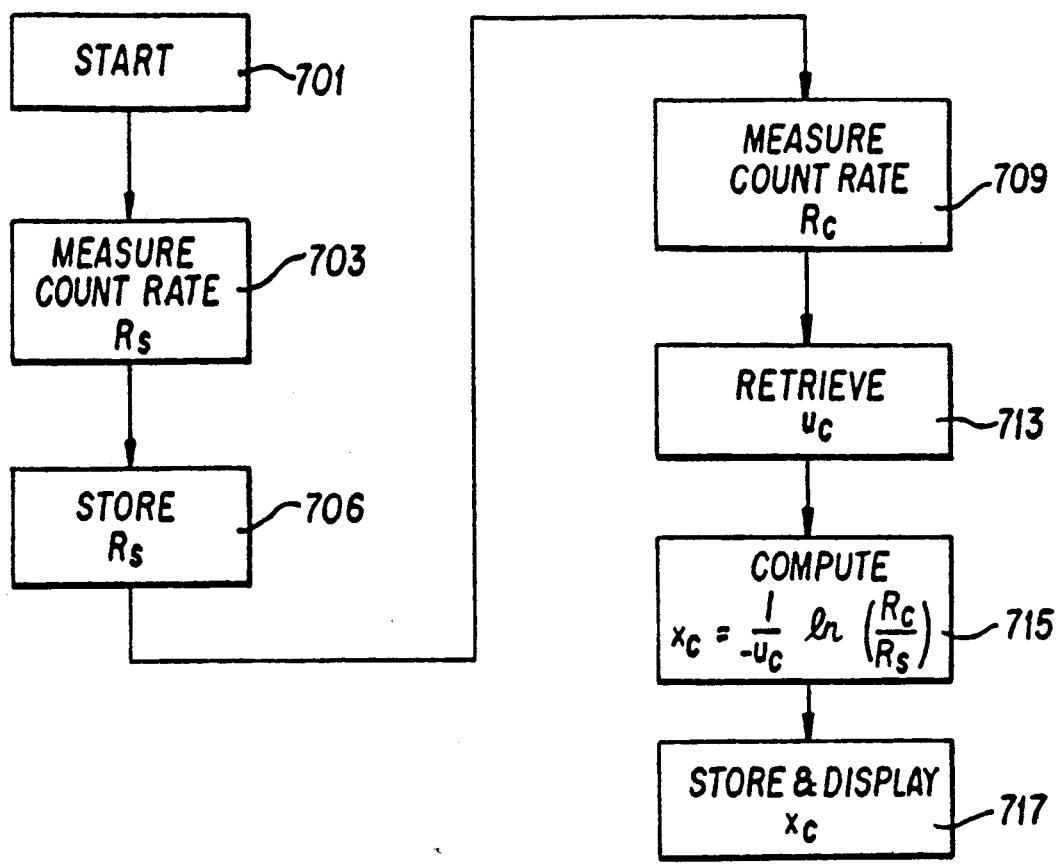
FIG. 14 illustrates in flow chart form a microprocessor program for measuring a coating thickness.

FIG. 14 is a flow chart for a microprocessor 13 which receives the count rate outputs from detectors 605 and 611 and which operates to determine a thickness of coating layer 610. The count rate outputs of respective detectors 605 and 611 are conveniently multiplexed to a single microprocessor 13. In step 703 the count rate value $R_s$ is taken from detector 605 and stored in step 706 following which the count rate value $R_c$ from detector 611 is taken and stored in step 709. In step 713 the value $R_s$ and previously stored value $u_c$, corresponding to the coating material, are retrieved and used in step 715 to calculate equation 14 following which in step 717 the calculated thickness value $x_c$ of the coating layer is stored and displayed.

In the above discussion of FIG. 12, it is assumed that detector/source pairs 605/607 and 611/613 are matched, that is, have the same particle radiation detecting and counting characteristics. If the detector/source pairs 605/607 and 611/613 are not matched, then their relative counting characteristics are measured and a correction factor is applied to one or the other of the count outputs of detector 605 or 611. This correction is done in FIG. 14 at either step 703 or step 709 where the count rates $R_s$, $R_c$ are measured. Typically, the correction is obtained by measuring a count value with both detectors and with nothing in the measuring gap, determining the difference in count values, determining the percentage of difference of one detector count value relative to that of the other detector and then applying this difference percentage to a detected count value of a detector during actual material measurements.

In some environments of material thickness gauging a web of material passing a thickness detector sometimes undergoes "flutter" where the material web moves up and down relative to a measuring detector. In transmission mode radiation thickness measurements, the web of material is placed in a gap between a source of radiation and the radiation detector (e.g., in the gap in FIGS. 1, 5, 6 and 8). Because the material being measured scatters some of the radiation from the radiation source, the radiation count rate at the detector will vary as the material moves up and down in the gap. Even though the material may be of constant thickness or density, the detected thickness or density value will change because the radiation count rate changes by the web fluctuations. The web "flutter" then becomes a source of undesirable measurement error.

Figure 15:
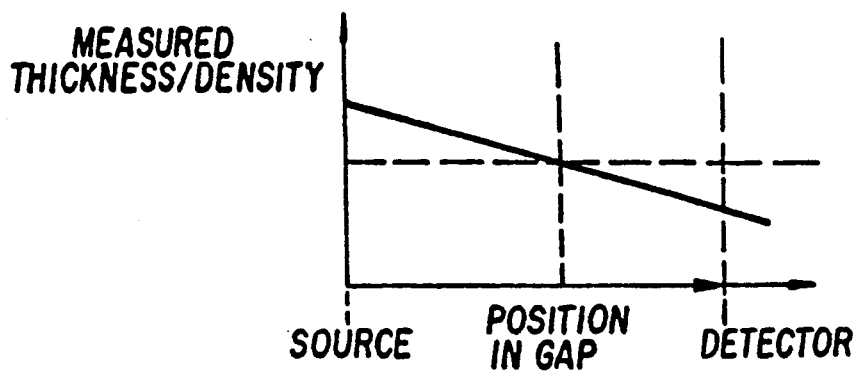
FIG. 15 is a graph useful in explaining the occurrence of flutter error in a measurement of web thickness.

If the measurement error caused by web "flutter" were plotted as a function of material position in the gap, for a sample of material of constant thickness or density, the relationship would be monotonic and will usually indicate a lower radiation count rate (or a greater thickness or density measurement) when the sample is closer to the source and farther from the detector; and a higher radiation count rate (or a lower thickness or density measurement) when the sample is farther from the source and closer to the detector. The actual amount of the change in a thickness or density radiation count rate will depend on several factors such as radiation size, gap size, detection area, etc. However, for a given fixed set of conditions, the "flutter" error is reproducible and may be illustrated by FIG. 15. As shown the erroneous measurement follows a generally linear relationship. If and indicated material thickness or density reading is denoted as I, the position of the material in the gap denoted as x, the slope of the FIG. 15 thickness/density graph denoted as m and the line intercept denoted as b, then $$I = T + e = mx + b \quad (15)$$

where I is the indicated thickness/density measurement, T is the true material thickness/density, and e is the error $(I-T=e)$.

One aspect of the present invention is to provide a system for compensation for flutter errors in thickness or density measurements of a moving web in a particle radiation detecting system.

Figure 16:
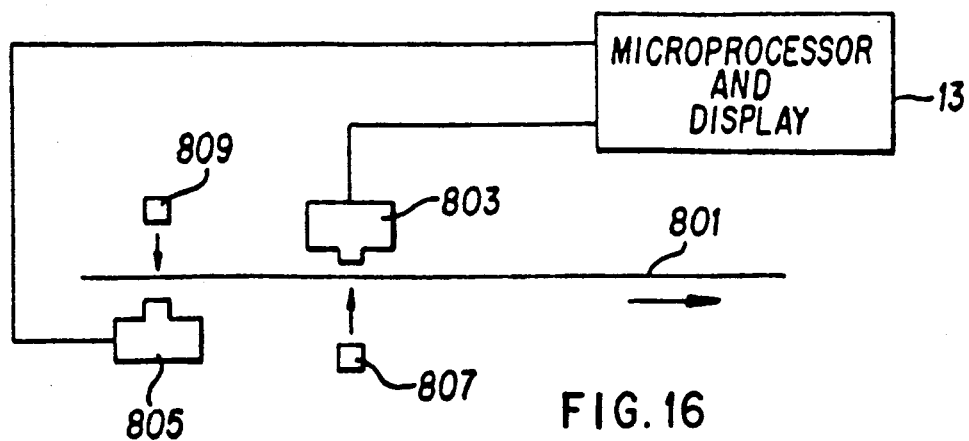
FIG. 16 illustrates a system for measuring the thickness or density of a material web and which also compensates for flutter errors.

FIG. 16 illustrates an embodiment of the invention in which two radiation detectors 803, 805 are disposed on opposite sides of a moving web 801 of a material, whose thickness or density is to be measured by radiation transmission from respective radiation sources 807, 809. The detectors 803, 805 are positioned sufficiently close together so that the material web may be considered as having the same true thickness or density inside the gap of each detector/source pair.

By having the detectors 803, 805 on opposite sides of the material web 801, the detector 805 will have a similar error in a detected thickness or density as the detector 803 as the web moves in the gap. The actual amount of error that detector 805 sees will be different from that seen by detector 803, but both errors will follow a linear relationship with different slope and intercept values. Because the invention employs a compact, low voltage and relatively inexpensive PIN diode type radiation detector, the detectors 803 and 805 can be stationarily mounted relatively close together, as shown in FIG. 16.

With detectors 803, 805 arranged in the fashion illustrated in FIG. 16, the unknown flutter error can be corrected out from a measured thickness or density to yield the true material thickness or density at any point in the gap. If the error indicated by the first and second detectors 803, 805 is $e_1$ and $e_2$ respectively, then $$e_1 = m_1 x + b_1 = T - I_1 \qquad (16)$$

and;

$$e_2 = m_2 x + b_2 = T - I_2 \qquad (17)$$

The true thickness or density T will be the same for each detector/source pair (803/807, 805/809) since the detectors 803, 805 are closely spaced.

Equations 16 and 17 can be combined and solved for x, the position in the gap, as follows:

$$e_1 = m_1 x + b_1 = (m_2 x + b_2) + I_2 - I_1 \qquad (18)$$

solving for x yields:

$$x = ((I_2 - I_1) + (b_2 - b_1)) / (m_1 - m_2) \qquad (19)$$

Now with x known, the error can be computed from either equation (16) or (17) as follows (using equation 16):

$$e_1 = m_1 x + b_1 \qquad (16)$$

then $$T = I_1 - e_1 \qquad (20)$$

which yields the true thickness or density measurement T.

If, in the simplest case, the slope and intercept of each source and detector pair yields a linear relationship which is the mirror image of the other source/detector pair (as would occur where the characteristics of each source/detector pair were identical) then the true value T of a measured thickness or density, defined as the measurement taken at the center of the gap, is given by averaging the two measured thickness or density values, i.e., $$T = (I_1 + I_2)/2.$$

Figure 17:
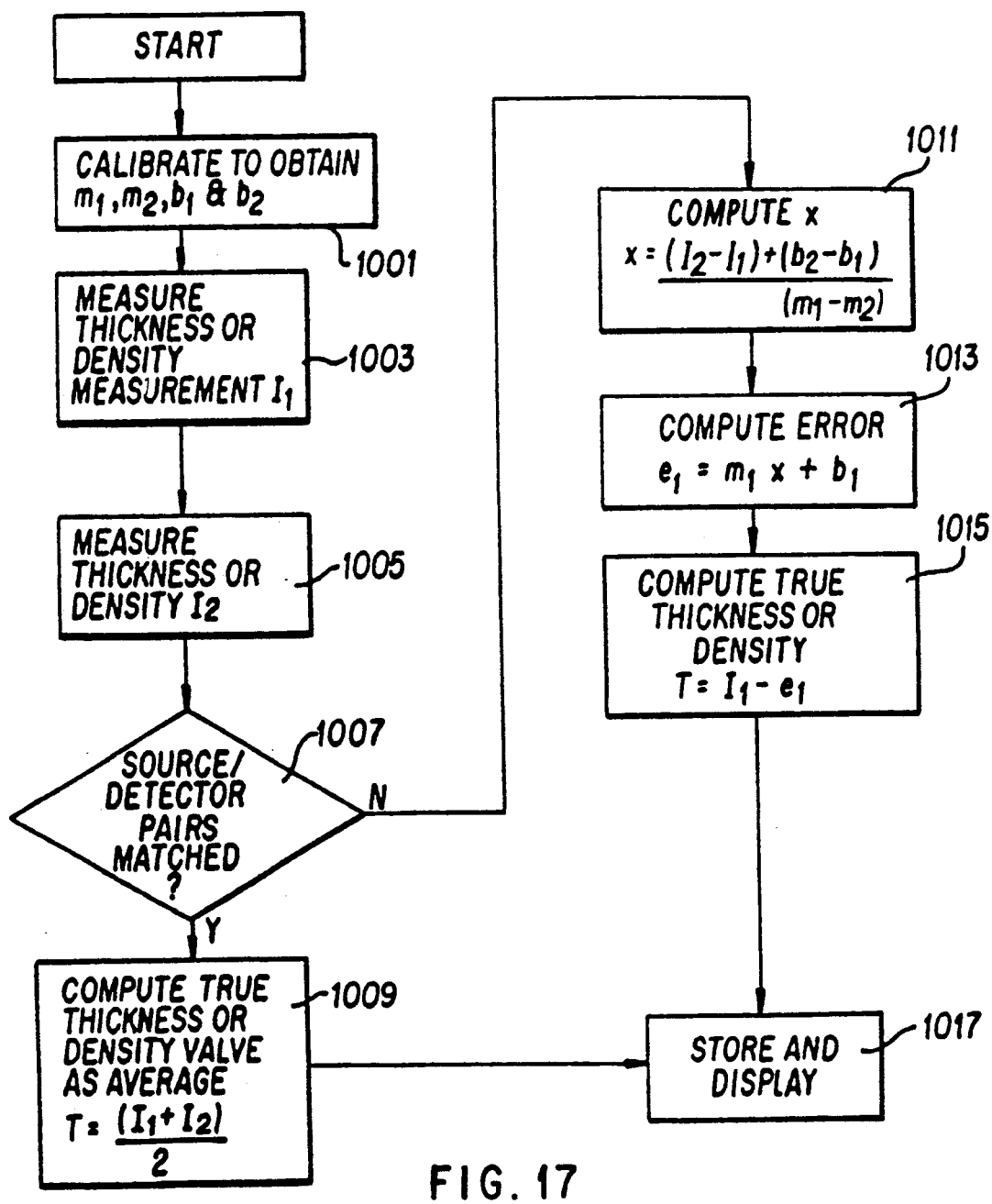
FIG. 17 illustrates in flow chart form a microprocessor program for providing a material web thickness or density measurement which is corrected for errors caused by web flutter.

FIG. 17 illustrates a flow chart for microprocessor 63 for correcting measured thickness or density errors following the above procedure. In step 1001 the system is calibrated to obtain the values $m_1$, $m_2$, $b_1$ and $b_2$. Since two detectors are involved, each must be calibrated to obtain $m_1$, $m_2$, $b_1$ and $b_2$. For each detector the calibration involves placing a material sample at two different locations (x) in the source-detector gap, and taking thickness or density measurements for each of the two locations. This will provide two points on the graph of measured thickness/density verses position in the gap illustrated in FIG. 15. From this linear graph a slope $m_1$ and intercept value $b_1$ can then be determined for detector 803 and like values $m_2$, $b_2$ can be determined for detector 805. Thereafter, in step 1003 a thickness or density measurement $I_1$ is made for one of the source/detector pairs (e.g. 807, 803) using the thickness or density measurement procedure described above in steps 123-127 of FIG. 2 (for thickness) or steps 123-127 of FIG. 10 (for density). Then a thickness or density measurement $I_2$ is made in step 1005 for the other source/detector pair (809, 805) using the same procedure. In step 1007 the microprocessor determines whether the source/detector pairs (807, 803 and 809, 805) are perfectly matched. This information is applied to the microprocessor from an external operator entered input at the front panel input device 71, such as a switch (e.g. "1" equals matched, "0" equals no match). If the source/detector pairs are matched then the microprocessor proceeds to step 1009 where it determines a true thickness or density value T by averaging the thickness or density measurements $(I_1 + I_2)/2$ which is then stored and displayed in step 1017.

If the source/detector pairs are not matched, the microprocessor proceeds to step 1011 where it computes the value x using equation 19 following which it proceeds to step 1013 where the error value $e_1$ is computed (equation 16). After this the true thickness or density value T is determined in step 1015 by computing equation 20 and this true value is stored and displayed in step 1017.

Thus far, the PIN diode particle radiation detector (FIG. 1) of the invention has been described with respect to measuring a thickness or density of an object or material. It is also possible to use the PIN diode particle radiation detector of the invention to measure the denier of a yarn and similar fibers. During the manufacture of yarns and other fibrous material and fibers such as rayon, nylon, silk, cotton, etc., it is desired to know the weight per unit length of the material. A unit of measure of the weight per unit length is denier. One denier equals 50 mg of material per 450 m of yarn or fiber. A knowledge of the denier of a fiber is useful in estimating the strength of the fiber, for controlling the manufacturing conditions of the fiber, for estimating fiber diameter and, in general, for quality control of the manufactured fiber.

Figure 18A:
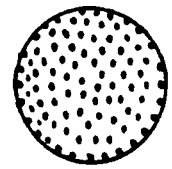
FIGS. 18A and 18B are cross-sectional views of a fiber bundle under different degrees of tension.
Figure 18B:

Conventionally, optical sensors have been used to measure denier with unreliable results mainly because the cross-sectional area of the yarn or fiber may vary widely while the denier remains constant. This is because the degree of compaction of a fiber which typically consists of a bundle of many small fibers can change due to the amount of tension it is under without significantly affecting the weight per unit length, as long as the individual small fibers are not stretched appreciably. This is illustrated in FIGS. 18A and 18B for a sample fiber formed of a bundle of the same number of smaller fibers. In FIG. 18A a much greater cross-section is evident than in FIG. 18B. Although the bundle diameter varies greatly, the denier may be the same for the FIG. 18A and 18B fiber bundles.

Capacitance techniques have also been tried to measure denier, but these suffer from their tendency to drift due to temperature and mechanical tolerances of the capacitance probes.

Figure 19:
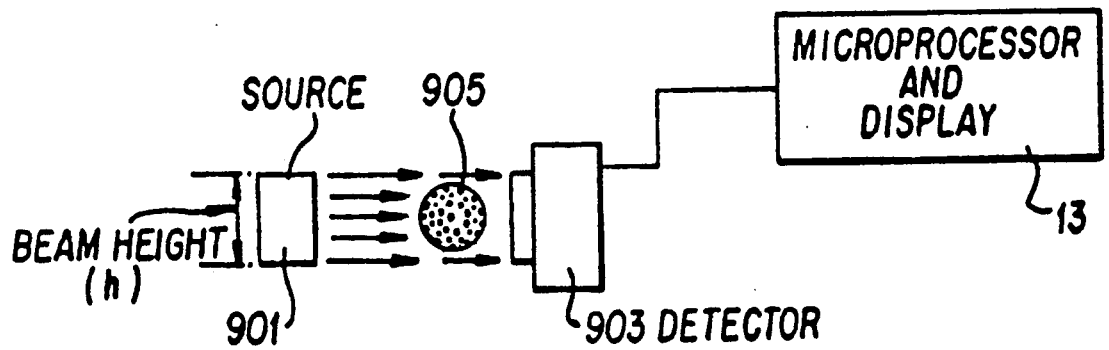
FIG. 19 illustrates in cross-sectional end view a system for measuring the denier of a fiber or yarn.
Figure 20:
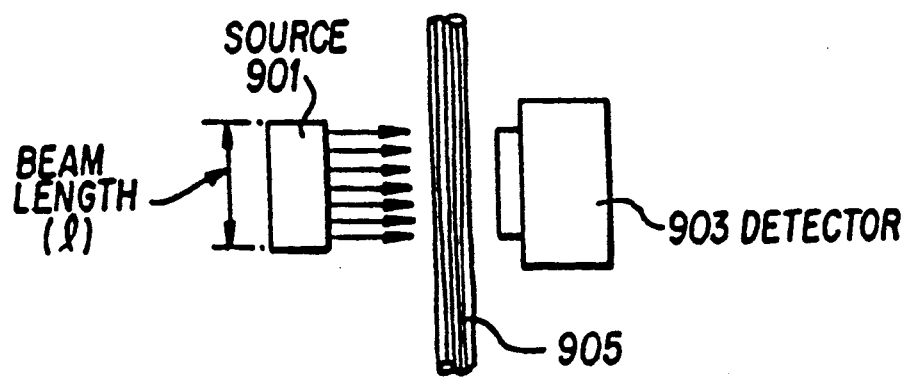
FIG. 20 illustrates in top view the system of FIG. 19.

The PIN diode radiation detector of FIG. 1 can be used to reliably measure denier of a yarn or fiber bundle. FIGS. 19 and 20 respectively show in cross-sectional and top plan views the use of a radiation source 901 and associated PIN diode detector 903 to measure denier of a yarn or fiber bundle 905. Detector 903 has electrical circuitry illustrated in FIG. 1. Radiation from source 901 can be used to measure denier of fiber bundle 905 since the radiation interacts with the total amount of matter in the beam path, irrespective of whether the fiber bundle 905 is tightly packed or not. As long as none of the fibers in the bundle extends outside the radiation beam in the cross-sectional view of FIG. 19, the radiation count rate will be responsive to and representative of the total amount of fiber mass in the beam. That is, that particle beam must have a sufficient height h to extend beyond the cross-section of the fiber or fiber bundle to be measured and the particle detector must have a detection area sufficiently large to detect the entirety of the beam height h. Since the beam is of a defined height (h in FIG. 19) and length (l in FIG. 20), the amount of mass that the fiber bundle 905 presents to the beam is directly proportional to the fiber bundle's weight per unit length which can be calibrated directly in units of denier.

Figure 21:
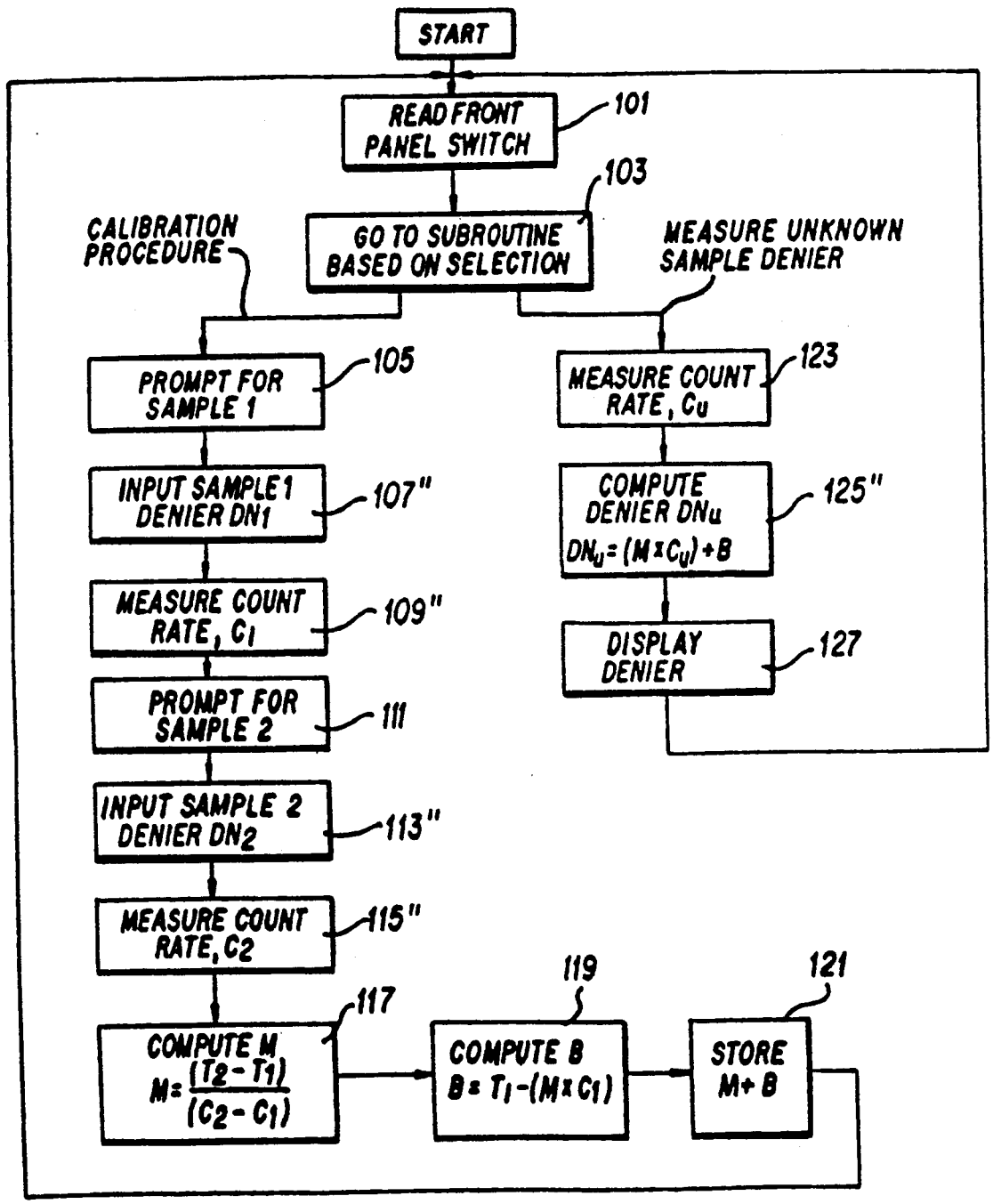
FIG. 21 illustrates in flow chart form a microprocessor program for providing a denier measurement.

FIG. 21 is a flow chart for microprocessor 63 for measuring denier. It is similar to the flow chart of FIG. 2 for a thickness measurement but minor changes have been made for denier measurement. Specifically, in steps 107″ and 113″ a first and second yarn or fiber sample is used to calibrate the measurement system. Otherwise the calibration procedure of FIG. 21 is the same as in FIG. 2.

Likewise, the actual denier measurement in steps 123, 125″ and 127 are similar to steps 123, 125 and 127 in FIG. 2, except in step 125″ a denier value $DN_u$ is computed.

In all of the embodiments of measurement systems described above, whether thickness, density or denier, it should be recognized that measured value may be displayed and/or used as a controlling signal to other processing devices.

While various embodiments of the present invention have been described and illustrated in connection with the drawings, it should be apparent that many modifications can be made to the invention as described, without departing from the spirit and scope of the invention. Accordingly, the invention is not limited by the foregoing description but is only limited by the scope of the claims appended hereto.

I claim:

1. A thickness/density measuring apparatus comprising:
   a particle radiation source;
   a particle radiation detector spaced from said source and comprising a PIN diode;
   means for preventing light from impinging on said diode, but permitting particle radiation from said source to strike said diode and for further providing a low resistance conductive material layer in a path of particle movement between said source and said detector;
   a charge sensitive preamplifier connected to an output of said diode;
   a first high pass filter connected to the output of said preamplifier;
   an operational amplifier connected to the output of said first high pass filter;
   a second high pass filter connected to the output of said amplifier;
   a comparator receiving the output of said second high pass filter and providing an output signal when the level of said second high pass filter output exceeds a set threshold; and
   means responsive to the output of said comparator for providing a signal representative of at least one of the thickness and density of a material placed between said particle radiation source and particle radiation detector.

2. A thickness/density measuring apparatus as in claim 1, wherein said providing means comprises a pulse rate counter coupled to the output of said comparator means and means responsive to the output of said pulse rate counter for producing said signal.

3. A thickness/density measuring apparatus as in claim 2, wherein said producing means comprises a microprocessor for converting a pulse count rate into said signal.

4. A thickness/density measuring apparatus as in claim 1, further comprising an opto-isolator for coupling the output of said comparator to said providing means.

5. A thickness/density measuring device as in claim 1, further comprising a power supply for supplying operating power to said diode, preamplifier, amplifier and comparator, said power supply comprising means for providing a first unregulated D.C. voltage of a first value and means for producing from said unregulated D.C. voltage a plurality of regulated D.C. voltages.

6. A thickness/density measuring apparatus as in claim 5, wherein said means for producing a plurality of regulated D.C. voltage comprises a transformer for receiving said unregulated D.C. voltage at a first primary winding thereof and for supplying said regulated D.C. voltages at a plurality of secondary windings, means for switching the current through said first primary winding, a pulse width modulator for operating said switching means, and means for coupling said pulse width modulator to a second primary winding of said transformer.

7. A thickness/density measuring apparatus comprising:
   a detector unit, a processing unit spaced from said detector unit and a communication link coupling said detector and processing units,
   said detector unit comprising:
   a housing having a light blocking, particle radiation permeable, window therein, said window including a low resistance conductive material layer;
   a flat area PIN diode mounted within said housing and adjacent said window for receiving particle radiation;

a charge sensitive preamplifier connected to the output of said PIN diode;

an operational amplifier coupled to the output of said preamplifier;

a high pass filter coupled to the output of said amplifier;

a comparator coupled to the output of said filter for comparing said filter output with a set threshold; and means for coupling the output of said comparator to an output terminal of said detector unit;

said processing unit comprising:

means for receiving the output of said comparator and for converting said comparator output to a measurement signal representing at least one of thickness and density of a material.

8. A thickness/density measuring apparatus as in claim 7, wherein said communications link is a wired connection between said detector unit and said processing unit.

9. A thickness/density measuring apparatus as in claim 7, wherein said processing unit further comprises means for displaying a representation of said measurement signal.

10. A thickness/density measuring apparatus as in claim 7, wherein said means for receiving and converting comprises a pulse rate counter coupled to the output of said comparator means and means responsive to the output of said pulse rate counter for producing said measurement signal.

11. A thickness/density measuring apparatus as in claim 10, wherein said producing means comprises a microprocessor for converting a pulse count rate into said measurement signal.

12. A thickness/density measuring apparatus as in claim 10, further comprising an opto-isolator for coupling the output of said comparator to said processing unit.

13. A thickness/density measuring device as in claim 7, further comprising a power supply for supplying operating power to said diode, preamplifier, amplifier and comparator, said power supply comprising means located in said processing unit for providing a first unregulated D.C. voltage of a first value; means located in said detector unit for producing from said unregulated D.C. voltage a plurality of regulated D.C. voltages, said communications link connecting said means for providing said first unregulated D.C. voltage with said means for producing a plurality of regulated D.C. voltages.

14. A thickness/density measuring apparatus as in claim 13, wherein said means for producing a plurality of regulated D.C. voltage comprises a transformer for receiving said unregulated D.C. voltage at a first primary winding thereof and for supplying said regulated D.C. voltages at a plurality of secondary windings, means for switching the current through said first primary winding, a pulse width modulator for operating said switching means, and means for coupling said pulse width modulator to a second primary winding of said transformer.

15. A thickness/density measuring apparatus comprising:

a particle radiation detector for receiving particle radiation, said detector comprising a PIN diode;

means for preventing light radiation from striking said diode, but permitting particle radiation to strike said diode and for further providing a low resistance conductive material layer in a path of particle movement toward said PIN diode;

a charge sensitive preamplifier coupled to the output of said PIN diode;

an amplifier coupled to the output of said preamplifier;

a comparator coupled to the output of said amplifier for providing an output signal when the level of the output of said amplifier exceeds a set threshold;

means responsive to the output of said comparator for providing a pulse rate signal; and meals for converting said pulse rate signal to one of a thickness or density measurement of a material which is positioned to affect the amount of radiation which reaches said detector from a particle radiation source.

16. A thickness/density measuring apparatus as in claim 15, further comprising a radiation source spaced from said detector.

17. A thickness/density measuring apparatus as in claim 16, wherein said detector is mounted in a housing and said source is mounted on an arm extending from said housing at a position to oppose said detector whereby a gap is formed between said source and detector for accommodating a material to be measured.

18. A thickness/density measuring apparatus as in claim 16, further comprising means for mounting said radiation source relative to said detector such that particle radiation detected by said detector is backscattered by said material to be measured.

19. A thickness/density measuring apparatus as in claim 16, wherein said detector is mounted within a housing behind a particle radiation permeable, light radiation-blocking window of said housing.

20. A thickness/density measuring apparatus as in claim 19, wherein said window is a thin film window.

21. A thickness/density measuring apparatus as in claim 20, wherein said window is formed of an aluminized mylar.

22. A thickness/density measuring apparatus as in claim 16, further comprising a first high pass filter connected between said preamplifier and amplifier.

23. A thickness/density measuring apparatus as in claim 22, further comprising a second high pass filter connected between said amplifier and comparator.

24. A thickness/density measuring apparatus as in claim 15, further comprising an opto-isolator connected between said comparator and said means providing a pulse rate signal.

25. A thickness/density measuring apparatus as in claim 15, wherein said apparatus is usable for a thickness measurement and further comprises means for calibrating said apparatus for a thickness measurement, said calibrating means comprising means for entering an actual thickness value ($T_s$) for a calibration material sample, means for determining a sample pulse count rate ($C_s$) for said material sample, means for storing the values ($C_s$) and ($T_s$), means for entering an indication of material type for a measured material, means for storing said entered material type, and means for storing a plurality of slope values (M) for various combinations of a sample pulse count rate ($C_s$), and entered actual thickness value ($T_s$) and an entered material type.

26. A thickness/density measuring apparatus as in claim 25, wherein said converting means comprises means for computing a thickness value in accordance with the following:

$$T_u = (M \times (C_u - C_s)) + T_s$$

where $T_u$ is the unknown thickness value, $C_u$ is the pulse rate signal, $T_s$ is the actual thickness of a material sample used for calibration, $C_s$ is the pulse count rate for said material sample, and M is a slope value selected from said plurality of slope values which correspond to an entered $T_s$ value, a determined $C_s$ value, and an entered material type.

27. A thickness/density measuring apparatus as in claim 15, wherein said PIN diode contains no protective layers between said preventing means and particle radiation sensitive areas thereof.

28. An extrusion film thickness control system comprising means for extruding a film thickness through a gap defined by pairs of die lips divided into a plurality of die lip sections along their length:
- a thickness measuring device for each die lip section, each measuring device comprising a particle radiation source; a particle radiation detector spaced from said source and comprising a PIN diode; means for preventing light radiation from striking said PIN diode, but permitting particle radiation to strike said diode, a charge sensitive preamplifier connected to an output of said diode; an amplifier coupled to the output of said preamplifier; a comparator coupled to the output of said amplifier and providing an output signal when the level of the output of said amplifier exceeds a set threshold; means responsive to the output of said comparator for providing a signal representative of the thickness of a material placed in a position to affect the radiation from said source which reaches said detector;
- means for separately controlling the gaps of each of said lip sections; and
- means for respectively associating an output of a measuring device with the control means for a respective die lip section which produces a section of film measured by the measuring device.

29. A control system as in claim 28, wherein said control means comprises, for each die lip section, a heated bolt driven by an output signal from a respective thickness measuring device.

30. A materials thickness control system comprising;
- means for continuously forming a material into at least one desired thickness;
- control means for controlling said forming means to produce at least one desired thickness in said material;
- at least one thickness measuring device for measuring the thickness of said formed material, each of said measuring devices being positioned downstream of said forming means, each said measuring device comprising:
- a particle radiation source; a particle radiation detector spaced from said source and comprising a PIN diode; means for preventing light radiation from striking said PIN diode, but permitting particle radiation to strike said diode, a charge sensitive preamplifier connected to an output of said diode; an amplifier coupled to the output of said preamplifier; a comparator coupled to the output of said amplifier and providing an output signal when the level of the output of said amplifier exceeds a set threshold; means responsive to the output of said comparator for providing a signal representative of the thickness of a material placed in a position to affect the radiation from said source which reaches said detector;
- said control means controlling said forming means in response to the signal representing thickness provided by at least one said measuring device.

31. A materials thickness control system as in claim 30, wherein said material is an extruded material and said forming means is an extruder.

32. A materials thickness control system as in claim 30, wherein said extruded material is an extruded film.

33. A materials thickness control system as in claim 31, wherein said forming means includes an extruder die.

34. A materials thickness control system as in claim 30, wherein, for each measuring device, said light preventing means is formed of a light blocking low resistance conductive material.

35. A material thickness control system as in claim 30, wherein said control means includes a PID controller.

36. A material thickness control system as in claim 30, further comprising plurality of said measuring devices spaced about a formed material, said control means being responsive to thickness representative signals from said plurality of spaced measuring devices.

* * * * *